United States Patent
Litherland et al.

(10) Patent No.: US 9,380,974 B2
(45) Date of Patent: *Jul. 5, 2016

(54) MULTI-SITE BODY FLUID SAMPLING AND ANALYSIS CARTRIDGE

(75) Inventors: Craig M. Litherland, Cupertino, CA (US); Jeffrey L. Emery, Redwood City, CA (US); Raul Escutia, Daly City, CA (US); James W. Pfeiffer, Los Gatos, CA (US); Jeffrey M. Jones, Sunnyvale, CA (US)

(73) Assignee: Intuity Medical, Inc., Sunnyvale, CA (US)

(*) Notice: Subject to any disclaimer, the term of this patent is extended or adjusted under 35 U.S.C. 154(b) by 1264 days.

This patent is subject to a terminal disclaimer.

(21) Appl. No.: 11/529,614

(22) Filed: Sep. 29, 2006

(65) Prior Publication Data

US 2007/0179405 A1 Aug. 2, 2007

Related U.S. Application Data

(60) Provisional application No. 61/721,966, filed on Sep. 30, 2005.

(51) Int. Cl.
*A61B 5/157* (2006.01)
*A61B 5/151* (2006.01)
(Continued)

(52) U.S. Cl.
CPC ............ *A61B 5/151* (2013.01); *A61B 5/1411* (2013.01); *A61B 5/1427* (2013.01);
(Continued)

(58) Field of Classification Search
CPC .......... A61B 5/150389; A61B 5/150396; A61B 5/150412; A61B 5/15045; A61B 5/151; A61B 5/15146; A61B 5/15148; A61B 5/150022; A61B 5/150969; A61B 5/15113; A61B 5/15117; A61B 5/15151; A61B 5/15153; A61B 5/15161; A61B 5/15163; A61B 5/155; A61B 5/157; A61B 5/1411
USPC .......................................... 600/583
See application file for complete search history.

(56) References Cited

U.S. PATENT DOCUMENTS

| 842,690 A | 1/1907 | Oswalt |
| D137,874 S | 5/1944 | Partridge |

(Continued)

FOREIGN PATENT DOCUMENTS

| CA | 2 513 465 A1 | 8/2004 |
| DE | 199 22 413 A1 | 11/2000 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.

(Continued)

*Primary Examiner* — Lee S Cohen
*Assistant Examiner* — Emily Lloyd
(74) *Attorney, Agent, or Firm* — Morrison & Foerster LLP

(57) ABSTRACT

An arrangement includes a housing, a plurality of sampling and analysis sites contained within the housing, each of the sampling and analysis sites having a skin-penetration member having a first end configured to pierce the skin, and an inner lumen in communication with the first end, an actuator operatively associated with the skin-penetration member, and an analyte quantification member in fluid communication with the inner lumen of the skin-penetration member. Integrated devices including such arrangements are also described.

40 Claims, 23 Drawing Sheets

(51) Int. Cl.
   *A61B 5/15*      (2006.01)
   *A61B 5/155*     (2006.01)
   *A61B 5/145*     (2006.01)
   *A61B 5/1486*    (2006.01)
   *A61B 5/00*      (2006.01)
   *G01N 21/03*     (2006.01)
   *A61B 5/1468*    (2006.01)

(52) U.S. Cl.
   CPC ............ *A61B 5/1468* (2013.01); *A61B 5/1486* (2013.01); *A61B 5/14532* (2013.01); *A61B 5/14546* (2013.01); *A61B 5/155* (2013.01); *A61B 5/157* (2013.01); *A61B 5/150022* (2013.01); *A61B 5/150068* (2013.01); *A61B 5/150076* (2013.01); *A61B 5/150083* (2013.01); *A61B 5/150099* (2013.01); *A61B 5/15111* (2013.01); *A61B 5/15113* (2013.01); *A61B 5/15117* (2013.01); *A61B 5/15121* (2013.01); *A61B 5/15123* (2013.01); *A61B 5/15146* (2013.01); *A61B 5/15148* (2013.01); *A61B 5/15151* (2013.01); *A61B 5/15161* (2013.01); *A61B 5/15163* (2013.01); *A61B 5/150167* (2013.01); *A61B 5/15186* (2013.01); *A61B 5/150229* (2013.01); *A61B 5/150343* (2013.01); *A61B 5/150389* (2013.01); *A61B 5/150396* (2013.01); *A61B 5/150412* (2013.01); *A61B 5/150946* (2013.01); *A61B 5/150954* (2013.01); *A61B 5/150984* (2013.01); *A61B 5/681* (2013.01); *A61B 5/6824* (2013.01); *A61B 5/6828* (2013.01); *G01N 21/0303* (2013.01); *A61B 5/150969* (2013.01); *A61B 2560/0443* (2013.01); *A61B 2560/0462* (2013.01)

(56) References Cited

U.S. PATENT DOCUMENTS

| | | | |
|---|---|---|---|
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A | 11/1971 | Sanz et al. |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 3,992,158 A | 11/1976 | Przybylowicz et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacornac |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | DeLuca et al. |
| 4,394,512 A | 7/1983 | Batz |
| 4,414,975 A | 11/1983 | Ryder et al. |
| 4,416,279 A | 11/1983 | Lindner et al. |
| 4,418,037 A | 11/1983 | Katsuyama et al. |
| 4,422,941 A | 12/1983 | Vaughan, Jr. et al. |
| 4,429,700 A | 2/1984 | Thees et al. |
| 4,627,445 A | 12/1986 | Garcia et al. |
| 4,637,403 A | 1/1987 | Garcia et al. |
| 4,637,406 A | 1/1987 | Guinn et al. |
| 4,653,513 A | 3/1987 | Dombrowski |
| 4,661,319 A | 4/1987 | Lape |
| 4,702,261 A | 10/1987 | Cornell et al. |
| 4,711,250 A | 12/1987 | Gilbaugh, Jr. et al. |
| 4,737,458 A | 4/1988 | Batz et al. |
| 4,767,415 A | 8/1988 | Duffy |
| 4,774,192 A | 9/1988 | Terminiello et al. |
| 4,790,979 A | 12/1988 | Terminiello et al. |
| 4,794,926 A | 1/1989 | Munsch et al. |
| 4,815,843 A | 3/1989 | Tiefenthaler et al. |
| 4,829,470 A | 5/1989 | Wang |
| 4,846,785 A | 7/1989 | Cassou et al. |
| 4,887,306 A | 12/1989 | Hwang et al. |
| 4,920,977 A | 5/1990 | Haynes |
| 4,930,525 A | 6/1990 | Palestrant |
| 4,935,346 A | 6/1990 | Phillips |
| 4,953,552 A | 9/1990 | De Marzo |
| 4,966,646 A | 10/1990 | Zdeblick |
| 4,995,402 A | 2/1991 | Smith et al. |
| 5,029,583 A | 7/1991 | Meserol |
| 5,049,487 A | 9/1991 | Phillips et al. |
| 5,050,617 A | 9/1991 | Columbus et al. |
| 5,059,394 A | 10/1991 | Phillips et al. |
| 5,077,199 A | 12/1991 | Basagni et al. |
| 5,094,943 A | 3/1992 | Siedel et al. |
| 5,116,759 A | 5/1992 | Klainer et al. |
| 5,131,404 A | 7/1992 | Neeley et al. |
| 5,141,868 A | 8/1992 | Shanks et al. |
| 5,145,565 A | 9/1992 | Kater et al. |
| 5,146,437 A | 9/1992 | Boucheron |
| 5,153,416 A | 10/1992 | Neeley |
| 5,164,575 A | 11/1992 | Neeley et al. |
| 5,166,498 A | 11/1992 | Neeley |
| 5,174,291 A | 12/1992 | Schoonen et al. |
| 5,176,632 A | 1/1993 | Bernardi |
| 5,179,005 A | 1/1993 | Phillips et al. |
| 5,183,741 A | 2/1993 | Arai et al. |
| 5,196,302 A | 3/1993 | Kidwell |
| 5,208,163 A | 5/1993 | Charlton et al. |
| 5,213,966 A | 5/1993 | Vuorinen et al. |
| 5,217,480 A | 6/1993 | Haber et al. |
| 5,218,966 A | 6/1993 | Yamasawa |
| 5,223,219 A | 6/1993 | Subramanian et al. |
| 5,234,818 A | 8/1993 | Zimmermann et al. |
| 5,241,969 A | 9/1993 | Carson et al. |
| 5,251,126 A | 10/1993 | Kahn et al. |
| D341,848 S | 11/1993 | Bigelow et al. |
| 5,275,159 A | 1/1994 | Griebel |
| 5,278,079 A | 1/1994 | Gubinski et al. |
| 5,288,646 A | 2/1994 | Lundsgaard et al. |
| 5,299,571 A | 4/1994 | Mastrototaro |
| 5,301,686 A | 4/1994 | Newman |
| 5,302,513 A | 4/1994 | Miike et al. |
| 5,304,468 A | 4/1994 | Phillips et al. |
| 5,306,623 A | 4/1994 | Kiser et al. |
| 5,308,767 A | 5/1994 | Terashima |
| 5,320,607 A | 6/1994 | Ishibashi |
| 5,354,537 A | 10/1994 | Moreno |
| 5,360,595 A | 11/1994 | Bell et al. |
| 5,368,047 A | 11/1994 | Suzuki et al. |
| 5,383,512 A | 1/1995 | Jarvis |
| 5,390,671 A | 2/1995 | Lord et al. |
| 5,399,316 A | 3/1995 | Yamada |
| 5,401,110 A | 3/1995 | Neeley |
| 5,402,798 A | 4/1995 | Swierczek et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |

(56) References Cited

U.S. PATENT DOCUMENTS

| | | | |
|---|---|---|---|
| 5,611,809 | A | 3/1997 | Marshall et al. |
| 5,624,458 | A | 4/1997 | Lipscher |
| 5,630,986 | A | 5/1997 | Charlton et al. |
| 5,632,410 | A | 5/1997 | Moulton et al. |
| 5,636,632 | A | 6/1997 | Bommannan et al. |
| 5,647,851 | A | 7/1997 | Pokras |
| 5,658,515 | A | 8/1997 | Lee et al. |
| 5,660,791 | A | 8/1997 | Brenneman et al. |
| 5,676,850 | A | 10/1997 | Reed et al. |
| 5,680,858 | A | 10/1997 | Hansen et al. |
| 5,681,484 | A | 10/1997 | Zanzucchi et al. |
| 5,682,233 | A | 10/1997 | Brinda |
| 5,697,901 | A | 12/1997 | Eriksson |
| 5,701,181 | A | 12/1997 | Boiarski et al. |
| 5,701,910 | A | 12/1997 | Powles et al. |
| 5,705,018 | A | 1/1998 | Hartley |
| 5,708,787 | A | 1/1998 | Nakano et al. |
| 5,715,417 | A | 2/1998 | Gardien et al. |
| 5,730,753 | A | 3/1998 | Morita |
| 5,735,273 | A | 4/1998 | Kurnik et al. |
| 5,736,103 | A | 4/1998 | Pugh |
| 5,741,211 | A | 4/1998 | Renirie et al. |
| 5,746,217 | A | 5/1998 | Erickson et al. |
| 5,746,720 | A | 5/1998 | Stouder, Jr. |
| 5,757,666 | A | 5/1998 | Schreiber et al. |
| 5,759,364 | A | 6/1998 | Charlton et al. |
| 5,766,066 | A | 6/1998 | Ranniger |
| 5,771,890 | A | 6/1998 | Tamada |
| 5,797,693 | A | 8/1998 | Jaeger |
| 5,801,057 | A | 9/1998 | Smart et al. |
| 5,807,375 | A | 9/1998 | Gross et al. |
| 5,820,570 | A | 10/1998 | Erickson et al. |
| 5,827,183 | A | 10/1998 | Kurnik et al. |
| 5,840,020 | A | 11/1998 | Heinonen et al. |
| 5,841,126 | A | 11/1998 | Fossum et al. |
| 5,843,692 | A | 12/1998 | Phillips et al. |
| 5,846,837 | A | 12/1998 | Thym et al. |
| 5,854,074 | A | 12/1998 | Charlton et al. |
| D403,975 | S | 1/1999 | Douglas et al. |
| 5,855,801 | A | 1/1999 | Lin et al. |
| 5,856,195 | A | 1/1999 | Charlton et al. |
| 5,858,194 | A | 1/1999 | Bell |
| 5,866,281 | A | 2/1999 | Guckel et al. |
| 5,871,494 | A | 2/1999 | Simons et al. |
| 5,879,310 | A | 3/1999 | Sopp et al. |
| 5,879,326 | A | 3/1999 | Godshall et al. |
| 5,879,367 | A | 3/1999 | Latterell et al. |
| 5,891,053 | A | 4/1999 | Sesekura |
| 5,893,870 | A | 4/1999 | Talen et al. |
| 5,911,711 | A | 6/1999 | Pelkey |
| 5,911,737 | A | 6/1999 | Lee et al. |
| 5,912,139 | A | 6/1999 | Iwata et al. |
| 5,925,021 | A | 7/1999 | Castellano et al. |
| 5,928,207 | A | 7/1999 | Pisano et al. |
| 5,930,873 | A | 8/1999 | Wyser |
| 5,938,679 | A | 8/1999 | Freeman et al. |
| 5,945,678 | A | 8/1999 | Yanagisawa |
| 5,951,492 | A | 9/1999 | Douglas et al. |
| 5,951,493 | A | 9/1999 | Douglas et al. |
| 5,954,685 | A | 9/1999 | Tierney |
| 5,962,215 | A | 10/1999 | Douglas et al. |
| 5,968,760 | A | 10/1999 | Phillips et al. |
| 5,968,765 | A | 10/1999 | Grage et al. |
| 5,971,941 | A | 10/1999 | Simons et al. |
| 5,972,294 | A | 10/1999 | Smith et al. |
| 5,986,754 | A | 11/1999 | Harding |
| 5,989,409 | A | 11/1999 | Kurnik et al. |
| 5,993,189 | A | 11/1999 | Mueller et al. |
| 6,001,067 | A | 12/1999 | Shults et al. |
| 6,005,545 | A | 12/1999 | Nishida et al. |
| 6,010,463 | A | 1/2000 | Lauks et al. |
| 6,010,519 | A * | 1/2000 | Mawhirt et al. ............... 606/181 |
| 6,014,135 | A | 1/2000 | Fernandes |
| 6,014,577 | A | 1/2000 | Henning et al. |
| 6,023,629 | A | 2/2000 | Tamada |
| 6,027,459 | A | 2/2000 | Shain et al. |
| 6,030,827 | A | 2/2000 | Davis et al. |
| 6,032,059 | A | 2/2000 | Henning et al. |
| 6,036,924 | A | 3/2000 | Simons et al. |
| 6,041,253 | A | 3/2000 | Kost et al. |
| 6,050,988 | A | 4/2000 | Zuck |
| 6,056,701 | A | 5/2000 | Duchon et al. |
| 6,056,734 | A | 5/2000 | Jacobsen et al. |
| 6,058,321 | A | 5/2000 | Swayze et al. |
| 6,059,815 | A | 5/2000 | Lee et al. |
| 6,061,128 | A | 5/2000 | Zweig et al. |
| 6,063,039 | A | 5/2000 | Cunningham et al. |
| 6,071,251 | A | 6/2000 | Cunningham et al. |
| 6,071,294 | A | 6/2000 | Simons et al. |
| 6,077,660 | A | 6/2000 | Wong et al. |
| 6,080,116 | A | 6/2000 | Erickson et al. |
| 6,083,196 | A | 7/2000 | Trautman et al. |
| 6,086,544 | A | 7/2000 | Hibner et al. |
| 6,090,790 | A | 7/2000 | Eriksson |
| 6,091,975 | A | 7/2000 | Daddona et al. |
| 6,093,156 | A | 7/2000 | Cunningham et al. |
| 6,097,831 | A | 8/2000 | Wieck et al. |
| 6,099,484 | A | 8/2000 | Douglas et al. |
| 6,100,107 | A | 8/2000 | Lei et al. |
| 6,102,933 | A | 8/2000 | Lee et al. |
| 6,103,033 | A | 8/2000 | Say et al. |
| 6,103,197 | A | 8/2000 | Werner |
| 6,106,751 | A | 8/2000 | Talbot et al. |
| 6,118,126 | A | 9/2000 | Zanzucchi |
| 6,120,676 | A | 9/2000 | Heller et al. |
| 6,123,861 | A | 9/2000 | Santini, Jr. et al. |
| 6,126,899 | A | 10/2000 | Woudenberg et al. |
| 6,132,449 | A | 10/2000 | Lum et al. |
| 6,139,562 | A | 10/2000 | Mauze et al. |
| 6,142,939 | A | 11/2000 | Eppstein et al. |
| 6,152,942 | A | 11/2000 | Brenneman et al. |
| 6,162,639 | A | 12/2000 | Douglas |
| 6,175,752 | B1 | 1/2001 | Say et al. |
| 6,176,865 | B1 | 1/2001 | Mauze et al. |
| 6,183,434 | B1 | 2/2001 | Eppstein et al. |
| 6,183,489 | B1 | 2/2001 | Douglas et al. |
| 6,187,210 | B1 | 2/2001 | Lebouiz et al. |
| 6,192,891 | B1 | 2/2001 | Gravel et al. |
| 6,200,296 | B1 | 3/2001 | Dibiasi et al. |
| 6,206,841 | B1 | 3/2001 | Cunningham et al. |
| 6,214,626 | B1 | 4/2001 | Meller et al. |
| 6,219,574 | B1 | 4/2001 | Cormier et al. |
| 6,228,100 | B1 | 5/2001 | Schraga |
| 6,230,051 | B1 | 5/2001 | Cormier et al. |
| 6,231,531 | B1 | 5/2001 | Lum et al. |
| 6,241,862 | B1 | 6/2001 | McAleer et al. |
| 6,242,207 | B1 | 6/2001 | Douglas et al. |
| 6,245,215 | B1 | 6/2001 | Douglas et al. |
| 6,251,083 | B1 | 6/2001 | Yum et al. |
| 6,251,260 | B1 | 6/2001 | Heller et al. |
| 6,254,586 | B1 | 7/2001 | Mann et al. |
| 6,255,061 | B1 | 7/2001 | Mori et al. |
| 6,256,533 | B1 | 7/2001 | Yuzhakov et al. |
| 6,268,162 | B1 | 7/2001 | Phillips et al. |
| 6,271,045 | B1 | 8/2001 | Douglas et al. |
| 6,272,364 | B1 | 8/2001 | Kurnik |
| 6,283,926 | B1 | 9/2001 | Cunningham et al. |
| 6,289,230 | B1 | 9/2001 | Chaiken et al. |
| 6,298,254 | B2 | 10/2001 | Tamada |
| 6,299,578 | B1 | 10/2001 | Kurnik et al. |
| 6,309,351 | B1 | 10/2001 | Kurnik et al. |
| D450,711 | S | 11/2001 | Istvan et al. |
| 6,312,612 | B1 | 11/2001 | Sherman et al. |
| 6,312,888 | B1 | 11/2001 | Wong et al. |
| 6,322,808 | B1 | 11/2001 | Trautman et al. |
| 6,329,161 | B1 | 12/2001 | Heller et al. |
| 6,331,266 | B1 | 12/2001 | Powell et al. |
| 6,332,871 | B1 | 12/2001 | Douglas et al. |
| 6,334,856 | B1 | 1/2002 | Allen et al. |
| 6,350,273 | B1 | 2/2002 | Minagawa et al. |
| 6,352,514 | B1 | 3/2002 | Douglas et al. |
| 6,356,776 | B1 | 3/2002 | Berner et al. |
| 6,358,265 | B1 | 3/2002 | Thorne, Jr. et al. |
| 6,364,890 | B1 | 4/2002 | Lum et al. |

(56) References Cited

U.S. PATENT DOCUMENTS

| | | |
|---|---|---|
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,740,800 B1 | 5/2004 | Cunningham |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,192,061 B2 | 3/2007 | Martin |
| D540,343 S | 4/2007 | Cummins |
| 7,223,365 B2 | 5/2007 | Von Der Goltz |
| 7,225,008 B1 * | 5/2007 | Ward et al. ............ 600/345 |
| 7,226,461 B2 | 6/2007 | Boecker et al. |
| 7,258,673 B2 * | 8/2007 | Racchini et al. ............ 600/583 |
| D551,243 S | 9/2007 | Young |
| 7,270,970 B2 | 9/2007 | Anderson et al. |
| 7,297,151 B2 | 11/2007 | Boecker et al. |
| 7,343,188 B2 | 3/2008 | Sohrab |
| 7,344,507 B2 | 3/2008 | Briggs et al. |
| 7,427,377 B2 | 9/2008 | Zanzucchi et al. |
| D599,373 S | 9/2009 | Kobayashi et al. |
| D601,578 S | 10/2009 | Poulet et al. |
| 7,682,318 B2 | 3/2010 | Alden et al. |
| 7,803,123 B2 | 9/2010 | Perez et al. |
| 7,887,494 B2 | 2/2011 | Emery et al. |
| D642,191 S | 7/2011 | Barnett et al. |
| D654,926 S | 2/2012 | Lipman et al. |
| 8,231,832 B2 | 7/2012 | Zanzucchi et al. |
| 8,298,255 B2 * | 10/2012 | Conway et al. ............ 606/182 |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,382,681 B2 | 2/2013 | Escutia et al. |
| D691,174 S | 10/2013 | Lipman et al. |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,060,723 B2 | 6/2015 | Escutia et al. |
| 9,095,292 B2 | 8/2015 | Zanzucchi et al. |
| 2001/0001034 A1 | 5/2001 | Douglas |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0083685 A1 | 5/2003 | Freeman et al. |
| 2003/0083686 A1 | 5/2003 | Freeman et al. |
| 2003/0116596 A1 | 6/2003 | Terasawa |
| 2003/0135166 A1 | 7/2003 | Gonnelli |
| 2003/0135333 A1 * | 7/2003 | Aceti et al. ............ 702/31 |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212347 A1 | 11/2003 | Sohrab |
| 2004/0010207 A1 | 1/2004 | Flaherty et al. |
| 2004/0030353 A1 | 2/2004 | Schmelzeisen-redeker et al. |
| 2004/0049219 A1 | 3/2004 | Briggs et al. |
| 2004/0059256 A1 | 3/2004 | Perez |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0096959 A1 | 5/2004 | Stiene et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | Levaughn et al. |
| 2004/0236251 A1 | 11/2004 | Roe et al. |
| 2004/0238675 A1 | 12/2004 | Banaszkiewicz et al. |
| 2005/0010134 A1 | 1/2005 | Douglas et al. |
| 2005/0015020 A1 | 1/2005 | LeVaughn et al. |
| 2005/0096686 A1 | 5/2005 | Allen |
| 2005/0106713 A1 | 5/2005 | Phan et al. |
| 2005/0159678 A1 | 7/2005 | Taniike et al. |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0277972 A1 | 12/2005 | Wong et al. |

(56) References Cited

U.S. PATENT DOCUMENTS

| | | |
|---|---|---|
| 2006/0008389 A1 | 1/2006 | Sacherer et al. |
| 2006/0036134 A1 | 2/2006 | Tarassenko et al. |
| 2006/0117616 A1 | 6/2006 | Jones et al. |
| 2006/0135873 A1 | 6/2006 | Karo et al. |
| 2006/0155317 A1 | 7/2006 | List |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0017824 A1 | 1/2007 | Rippeth et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0179404 A1 | 8/2007 | Escutia et al. |
| 2007/0255181 A1 | 11/2007 | Alvarez-icaza et al. |
| 2007/0255302 A1 | 11/2007 | Koeppel et al. |
| 2008/0046831 A1 | 2/2008 | Imai et al. |
| 2008/0077048 A1 | 3/2008 | Escutia et al. |
| 2008/0194934 A1 | 8/2008 | Ray et al. |
| 2009/0156923 A1 | 6/2009 | Power et al. |
| 2010/0021948 A1 | 1/2010 | Lipman et al. |
| 2010/0095229 A1 | 4/2010 | Dixon et al. |
| 2010/0185120 A1 | 7/2010 | Sacherer et al. |
| 2011/0201909 A1 | 8/2011 | Emery et al. |
| 2012/0166090 A1 | 6/2012 | Lipman et al. |
| 2013/0158430 A1 | 6/2013 | Aceti et al. |
| 2013/0158432 A1 | 6/2013 | Escutia et al. |
| 2013/0172698 A1 | 7/2013 | Reynolds et al. |
| 2013/0274568 A1 | 10/2013 | Escutia et al. |
| 2014/0316301 A1 | 10/2014 | Escutia et al. |
| 2014/0376762 A1 | 12/2014 | Lipman et al. |

FOREIGN PATENT DOCUMENTS

| | | |
|---|---|---|
| DE | 103 02 501 A1 | 8/2004 |
| EP | 0 103 426 A2 | 3/1984 |
| EP | 0 255 338 A2 | 2/1988 |
| EP | 0 256 806 A2 | 2/1988 |
| EP | 0 396-016 A2 | 11/1990 |
| EP | 0 396-016 A3 | 11/1990 |
| EP | 1 266-607 A2 | 12/2002 |
| EP | 1 266-607 A3 | 12/2002 |
| EP | 1 360 934 A1 | 11/2003 |
| EP | 1 486-766 A1 | 12/2004 |
| EP | 1 486-766 B1 | 12/2004 |
| EP | 1 529-489 A1 | 5/2005 |
| EP | 1 529-489 B1 | 5/2005 |
| EP | 1 769-735 A1 | 4/2007 |
| JP | 63-305841 A | 12/1988 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-266889 A | 10/1997 |
| JP | 9-294737 A | 11/1997 |
| JP | 9-313465 A | 12/1997 |
| JP | 10-024028 A | 1/1998 |
| JP | 10-505258 A | 5/1998 |
| JP | 10-318970 A | 12/1998 |
| JP | 2000-126161 A | 5/2000 |
| JP | 2000-168754 A | 6/2000 |
| JP | 2000-254111 A | 9/2000 |
| JP | 2001-159618 A | 6/2001 |
| JP | 2001-515203 A | 9/2001 |
| JP | 2001-305096 A | 10/2001 |
| JP | 2001-330581 A | 11/2001 |
| JP | 2002-502045 A | 1/2002 |
| JP | 2002-514453 A | 5/2002 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-522500 A | 7/2004 |
| JP | 2004-528936 A | 9/2004 |
| JP | 2005-503538 A | 2/2005 |
| JP | 2005-087613 A | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-512969 A | 4/2006 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-521031 A | 8/2007 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-98/31275 A1 | 7/1998 |
| WO | WO-98/35225 A1 | 8/1998 |
| WO | WO-99/12008 A1 | 3/1999 |
| WO | 99/44508 A1 | 9/1999 |
| WO | WO-99/58051 A1 | 11/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/36400 A1 | 6/2000 |
| WO | WO-00/42422 A1 | 7/2000 |
| WO | WO-00/74763 A1 | 12/2000 |
| WO | WO-00/74763 A2 | 12/2000 |
| WO | WO-00/78208 A1 | 12/2000 |
| WO | WO-01/16575 A1 | 3/2001 |
| WO | WO-01/52727 A1 | 7/2001 |
| WO | 01/64105 A1 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91964 A3 | 12/2001 |
| WO | 02/00101 A2 | 1/2002 |
| WO | 02/49507 A1 | 6/2002 |
| WO | WO-02/49509 A2 | 6/2002 |
| WO | WO-02/49509 A3 | 6/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/030984 A1 | 4/2003 |
| WO | WO-03/066128 A2 | 8/2003 |
| WO | WO-03/066128 A3 | 8/2003 |
| WO | WO-03/070099 A1 | 8/2003 |
| WO | WO-03/071940 A1 | 9/2003 |
| WO | WO-03/071940 C1 | 9/2003 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2004/085995 A2 | 10/2004 |
| WO | WO-2004/085995 A3 | 10/2004 |
| WO | WO 2004105827 A2 * | 12/2004 |
| WO | WO-2005/006939 A2 | 1/2005 |

(56) References Cited

FOREIGN PATENT DOCUMENTS

| WO | WO-2005/006939 A3 | 1/2005 |
|---|---|---|
| WO | WO-2005/009238 A1 | 2/2005 |
| WO | WO 2005/009238 A1 | 2/2005 |
| WO | WO-2005/018709 A2 | 3/2005 |
| WO | WO-2005/018709 A3 | 3/2005 |
| WO | WO-2005/018710 A2 | 3/2005 |
| WO | WO-2005/018710 A3 | 3/2005 |
| WO | WO-2005/084546 A2 | 9/2005 |
| WO | WO-2005/084546 A3 | 9/2005 |
| WO | WO-2005/085995 A1 | 9/2005 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |

OTHER PUBLICATIONS

ADA (Jan. 1994). "Self-Monitoring of Blood Glucose," Consensus Statement *Diabetes Care* 17(1):81-86.
Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.
Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.
Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.
Chase, H.P. et al. (Feb. 2001). "Continuous Subcutaneous Glucose Monitoring in Children with Type 1 Diabetes," *Pediatrics* 107(2):222-226.
Clarke, W.L. et al. (Sep.-Oct. 1987). "Evaluating Clinical Accuracy of Systems for Self-Monitoring of Blood Glucose," *Diabetes Care* 10(5):622-628.
Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.
Coster, S. et al. (2000). "Monitoring Blood Glucose Control in Diabetes Mellitus: A Systematic Review." *Health Technology Assessment* 4(12):1-93.
Cox, D.J. et al. (Jun. 1997). "Understanding Error Grid Analysis," *Diabetes Care* 20(6):911-912.
D'Arrigo, T.D. (Mar. 2000). "GlucoWatch Monitor Poised for Approval," *Diabetes Forecast*, 53(3):43-44.
European Office Action mailed on Jan. 7, 2014 for EP Patent Application No. 12192620.8, filed on Nov. 14, 2012, 6 pages.
Extended European Search Report mailed on Apr. 29, 2013 for EP Patent Application No. 12192620.8, filed on Nov. 14, 2012, 8 pages.
Feldman, B. et al. (2000). "FreeStyle™: A Small-Volume Electrochemical Glucose Sensor for Home Blood Glucose Testing," *Diabetes Technology and Therapeutics*, 2(2):221-229.
International Search Report mailed on May 2, 2007, for PCT Application No. PCT/US2006/37923, filed on Sep. 9, 2006, 1 page.
Johnson, R.N. et al. (Jan. 1998). "Accuracy of Devices Used for Self-Monitoring of Blood Glucose," *Annals of Clinical Biochemistry* 35(1):68-74.

Johnson, R.N. et al. (Jan. 1999). "Analytical Error of Home Glucose Monitors: A Comparison of 18 Systems," *Annals of Clinical Biochemistry* 36(1):72-79.
Johnson, R.N. et al. (2001). "Error Detection and Measurement in Glucose Monitors," *Clinica Chimica Acta* 307:61-67.
Kumetrix, Inc. (Dec. 1999). "Painless Blood Glucose Monitoring, Courtesy of the Mosquito," *Start-Up* pp. 27-28.
Lee, S-C. (Jun. 1999). "Light Scattering by Closely Spaced Parallel Cylinders Embedded in a Finite Dielectric Slab," *Journal of the Optical Society of America A* 16(6):1350-1361.
McGarraugh, G. et al. (2001). "Physiological Influences on Off-Finger Glucose Testing," *Diabetes Technology & Therapeutics* 3(3):367-376.
McNichols, R.J. et al. (Jan. 2000). "Optical Glucose Sensing in Biological Fluids: An Overview," *Journal of Biomedical Optics*, 5(1):5-16.
Mahler, R.J. et al. (1999). "Clinical Review 102, Type 2 Diabetes Mellitus: Update on Diagnosis Pathophysiology, and Treatment," *The Journal of Clinical Endocrinology and Metabolism* 84(4):1165-1171.
Medline Plus. (Jun. 17, 2008). Medical Encyclopedia, Monitor Blood Glucose-Series: Part 1-4, 6 pages.
Neeley, W.E. et al. (1981). "An Instrument for Digital Matrix Photometry," *Clinical Chemistry* 27(10):1665-1668.
Neeley, W.E. (1983). "Reflectance Digital Matrix Photometry," *Clinical Chemistry* 29(6):1038-1041.
Neeley, W.E. (1983). "Multilayer Film Analysis for Glucose in 1- µL Samples of Plasma," *Clinical Chemistry* 29(12):2103-2105.
Neeley, W.E. (1988). "A Reflectance Photometer with a Square Photodiode Array Detector for Use on Multilayer Dry-Film Slides," *Clinical Chemistry* 34(11):2367-2370.
Otto, E. et al. (2000). "An Intelligent Diabetes Software Prototype: Predicting Blood Glucose Levels and Recommending Regimen Changes," *Diabetes Technology and Therapeutics* 2(4):569-576.
Pfohl, M. et al. (2000). "Spot Glucose Measurement in Epidermal Interstitial Fluid-An Alternative to Capillary Blood Glucose Estimation," *Experimental and Clinical Endocrinology & Diabetes* 108(1):1-4.
Princen, H.M. (May 1969). "Capillary Phenomena in Assemblies of Parallel Cylinders, I. Capillary Rise Between Two Cylinders," *Journal of Colloid and Interface Science* 30(1):69-75.
Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Rosen, S. (1999). "Road to New-Age Glucose Monitoring Still Rocky," *Diagnostic Insight*, pp. 4-5, 12-13, 16.
Smart, W.H. et al. (2000). "The Use of Silicon Microfabrication Technology in Painless Glucose Monitoring," *Diabetes Technology & Therapeutics* 2(4):549-559.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Trinder, P. (1969). "Determination of Glucose in Blood Using Glucose Oxidase with an Alternate Oxygen Acceptor," *Annals of Clinical Biochemistry* 6:24-28.
Written Opinion mailed on May 2, 2007, for PCT Application No. PCT/US2006/37923, filed on Sep. 9, 2006, 5 pages.
Yum, S. I. et al. (Nov. 1, 1999). "Capillary Blood Sampling for Self-Monitoring of Blood Glucose," *Diabetes Technology & Therapeutics*, 1(1):29-37.
Extended European Search Report mailed on Feb. 2, 2016 for European Patent Application No. 15187274.4, filed on Sep. 29, 2015, 5 pages.

\* cited by examiner

MULTI-SITE BODY FLUID SAMPLING AND ANALYSIS CARTRIDGE

The present application claims priority pursuant to 35 U.S.C. §119 to U.S. Patent Application Ser. No. 60/721,966 filed Sep. 30, 2005, the entire content of which is incorporated herein by reference.

FIELD

The present invention relates to devices, arrangements and methods for facilitating the sampling, collection and analysis of body fluids. In certain embodiments, the present invention can be directed to a cartridge that can be utilized in conjunction with an integrated body fluid sampling and monitoring devices.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

According to the American Diabetes Association, diabetes is the fifth-deadliest disease in the United States and kills more than 213,000 people a year, the total economic cost of diabetes in 2002 was estimated at over $132 billion dollars. One out of every 10 health care dollars is spent on diabetes and its complications. The risk of developing type I juvenile diabetes is higher than virtually all other chronic childhood diseases. Since 1987 the death rate due to diabetes has increased by 45 percent, while the death rates due to heart disease, stroke, and cancer have declined.

A critical component in managing diabetes is frequent blood glucose monitoring. Currently, a number of systems exist for self-monitoring by the patient. Most fluid analysis systems, such as systems for analyzing a sample of blood for glucose content, comprise multiple separate components such as separate lancing, transport, and quantification portions. These systems are bulky, complicated and confusing for the user. The systems require significant user intervention to perform repeated testing.

Some attempts have been made to integrate some or all of these functions. For instance, a device has been developed that contains a disposable array of test strips. This device integrates the functions of transport and quantification only. Another device attempts to integrate all three of the above-mentioned functions. However this device is single use, and the user must reload a test strip and lancet for each test. The device is also very large and requires significant user intervention. For instance, this device has separate members to create and to transport a sample. The wound is created with a lancet and a test strip collects a sample. This system uses several complicated mechanisms to bring the test strip to a position where it can collect the sample. Finally, the device is not configured for fingertip testing.

Another device contains an array of quantification strips and dispenses one strip at a time, without the function of automated lancing or sample transport.

Yet another device includes a disposable insert that may contain an array of lancets and possibly test strips. Yet the device is large, cumbersome, and non-wearable. The device may be expensive.

In addition, in those devices where such integration has been attempted, the mechanism(s) for actuating the skin-piercing members are provided in the reusable portion of the device and not in the cartridge. These actuation mechanisms are overly complex and bulky so that their inclusion into a disposable cartridge has been impractical.

In summary, most current systems that are not integrated involve many pieces that are not convenient and make the test difficult to perform discreetly. Other current devices may be somewhat integrated but still require significant user intervention, are not discreet, are overly complex and bulky and require more than one device to complete the test.

SUMMARY OF THE INVENTION

According to the present invention, there are provided body fluid sampling and monitoring devices and methods that may address one or more of the shortcomings noted above associated with conventional arrangements and devices.

Although not required, the present invention can provide devices, arrangements and techniques which possess one or more of the following advantages:

Convenience and Simplicity—according to the principles of the present invention the user can carry a single disposable cartridge which is capable of completing multiple tests.

Reduced Risk of Infection and Cross-Contamination—a cartridge formed according to the present invention ensures that the user cam can access a fresh lancet and test strip for every testing event, and that contaminated articles are contained and stored within the cartridge which acts like a self-contained receptacle.

Reduced Environmental Contamination of the Reagent—conventional systems protect test strips from environmental contamination by storing them in a plastic vial or other container. As soon as this container is opened, all the strips are exposed to the environment. This exposure can result in deterioration of the reagent contained in the test strips. According to the present invention, each reagent-containing test strip can be shielded from the environment in a chambers formed within the cartridge.

Improved Reliability—rather than relying on intervention by the user to deliver a sample to an analysis site (e.g., test strip), the present invention can automatically transfer a sample body fluid to an analysis site.

Automatic Calibration and Accuracy Verification—conventional systems typically require the user to input a calibration code for each new series of test strips. This procedure can be confusing and is often performed incorrectly, or ignored by the user. According to the present invention, calibration information will be provided on each cartridge and automatically read by an integrated meter or device upon insertion of the cartridge therein. Similarly, each cartridge can comprise one or more analysis sites which act as a control. For example, upon reading and analyzing the control representing a known concentration of analyte, the results obtained by the integrated meter are then compared to this known concentration. Any deviation therefrom can be accounted for and corrected by, for example, updating or modifying the algorithm utilized to calculate the concentration of analyte contained in the sample body fluid.

Automatic Algorithm and Software Update Capabilities—the cartridge of the present invention may include the readable information (e.g., in the form of a chip) which can be utilized to automatically update the software, firmware, algorithm and/or analysis method of the integrated meter or device upon insertion of the cartridge therein.

As used herein "digital" or "digit" means fingers or toes. "Digital body fluid" means expression of body fluid from a wound created on the fingers or toes, and encompasses lancing sites on the dorsal or palm side of the distal finger tips.

As used herein "alternate-site" means a location on the body other than the digits, for example, the palm, forearm or thigh. "Alternate-site body fluid sampling" means expression of body fluid from the lancing site on a surface of the body other than the fingers or toes, and encompasses lancing sites on the palm, forearm, and thigh.

As used herein, "body fluid" encompasses whole blood, intestinal fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid.

According to one aspect, the present invention is directed to an arrangement comprising: a housing; a plurality of sampling and analysis sites contained within the housing, each of the sampling and analysis sites comprising: a skin-penetration member having a first end configured to pierce the skin, and a inner lumen in communication with the first end; an actuator operatively associated with the skin-penetration member; and an analyte quantification member in fluid communication with the inner lumen of the skin-penetration member.

According to another aspect, the present invention is directed to an integrated meter or device comprising the above-identified arrangement.

BRIEF DESCRIPTION OF THE DRAWING FIGURES

The following description of preferred embodiments can be read in connection with the accompanying drawings in which like numerals designate like elements and in which.

DETAILED DESCRIPTION

According to a first aspect of the present invention, there are provided arrangements and techniques for sampling and analyzing body fluid to determine a concentration of a target analyte contained therein. Target analytes include, but are not limited to, glucose, bilirubin, alcohol, controlled substances, toxins, hormones, proteins, etc. The arrangements and techniques are suitable for use in sampling body fluid from a digit or from an alternate site.

Generally, the arrangement of the present invention may comprise a disposable arrangement. The disposable arrangement may be in the form of a cartridge. The present invention may also comprise an integrated meter comprising a disposable arrangement (e.g., cartridge) as well as a reusable portion. The cartridge may include an array of skin piercing elements attached to guides, triggers and/or actuation mechanisms. The cartridge may also include mechanisms for transporting a sample of body fluid from the skin surface into other areas of the device. According to certain embodiments, at least a portion of the transport operation is integrated into the skin-piercing elements. The cartridge may also include analyte quantification members that may be separate from or integrated with the transport member. The analyte quantification members may be designed to optically or electrochemically indicate detectable changes when exposed to the analyte of interest. The cartridge may also include one or more skin-interfacing members, possibly a soft silicone footprint. The skin interfacing member(s) or footprint(s) can optionally be constructed of any material that facilitates sample acquisition via conditioning the skin prior to, during and/or after piercing. Alternatively, the skin interface member(s) may be included in the reusable portion of the device. The disposable portion may include an energy source. The disposable portion may also include a housing designed to enclose, and/or seal the analyte medium. The disposable portion may also include mechanisms, or be designed to allow for user-adjustable skin piercing depth. The disposable portion may also include vacuum chambers as well as a means to provide an airtight seal against the skin. Finally, the disposable portion may contain readable information usable for calibration, control or software updating purposes.

An arrangement formed according to one exemplary embodiment of the present invention is illustrated in FIGS. 1-6. As illustrated therein, the arrangement can be provided generally in the form of a replaceable cartridge 10. The cartridge 10 comprises a housing 12. The housing 12 can be constructed of any suitable material. For example, a housing 12 can be constructed of a molded polymeric material.

Figure 1:
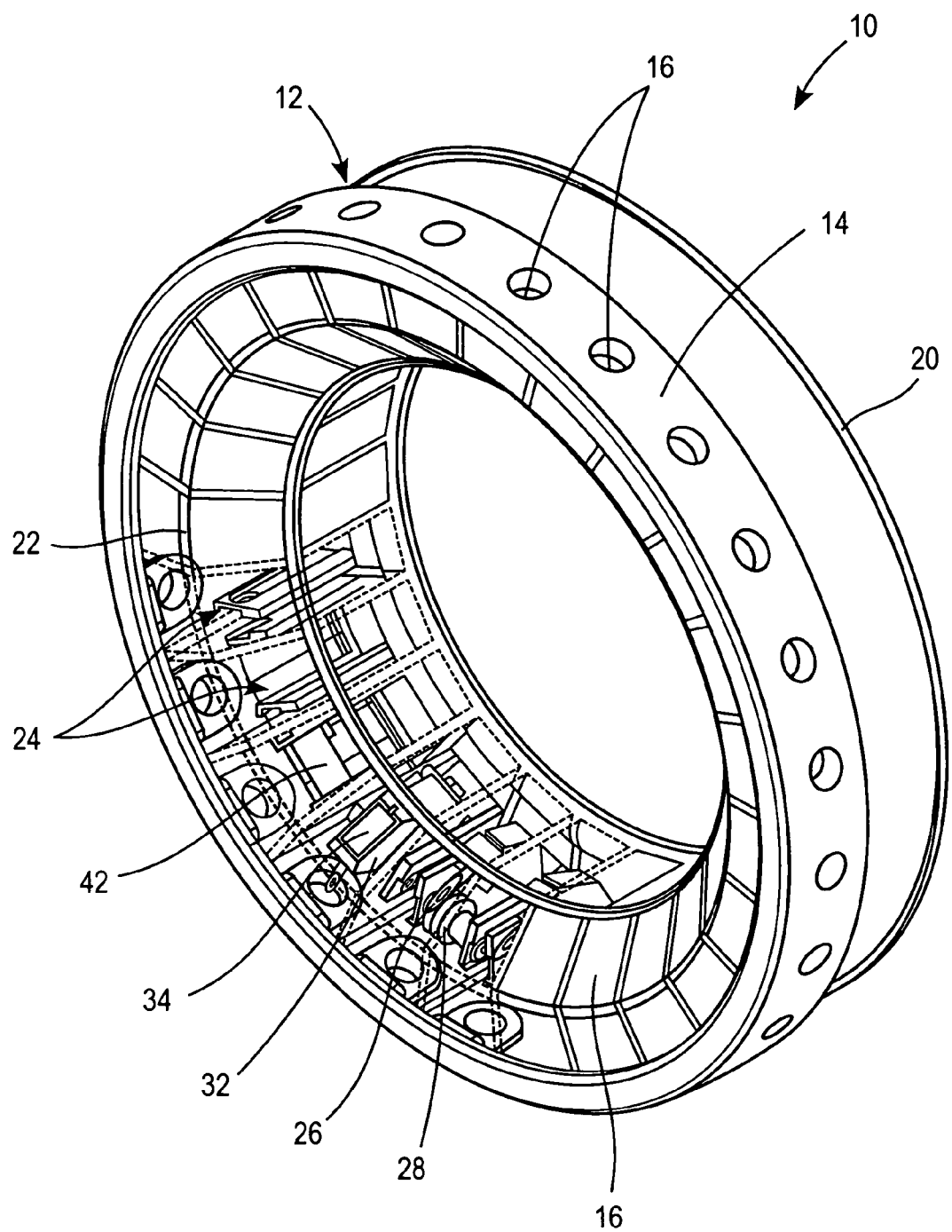
FIG. 1 is a perspective view of an arrangement constructed according to the present invention.
Figure 2:
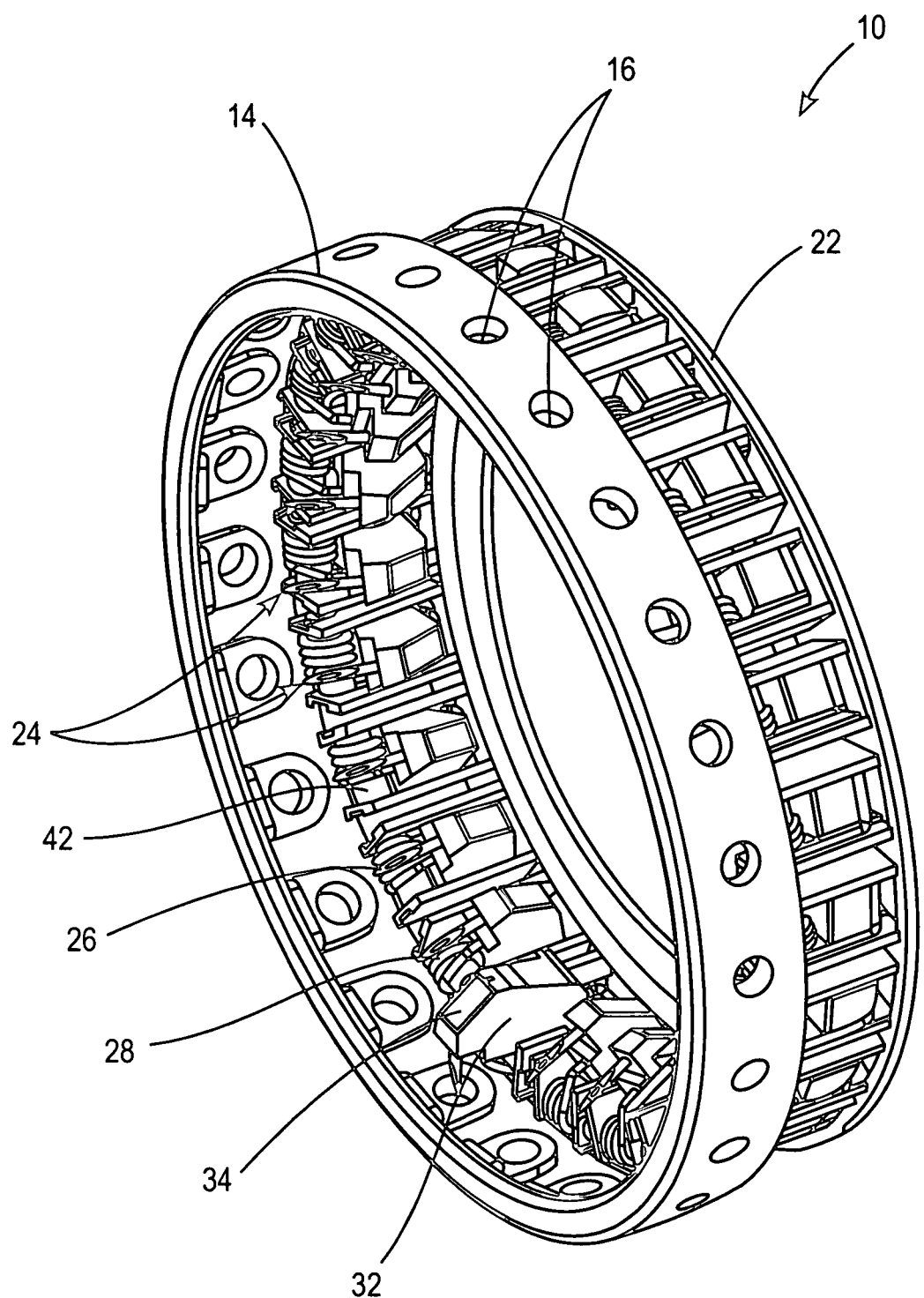
FIG. 2 is perspective view of a portion of the arrangement of FIG. 1.
Figure 3:
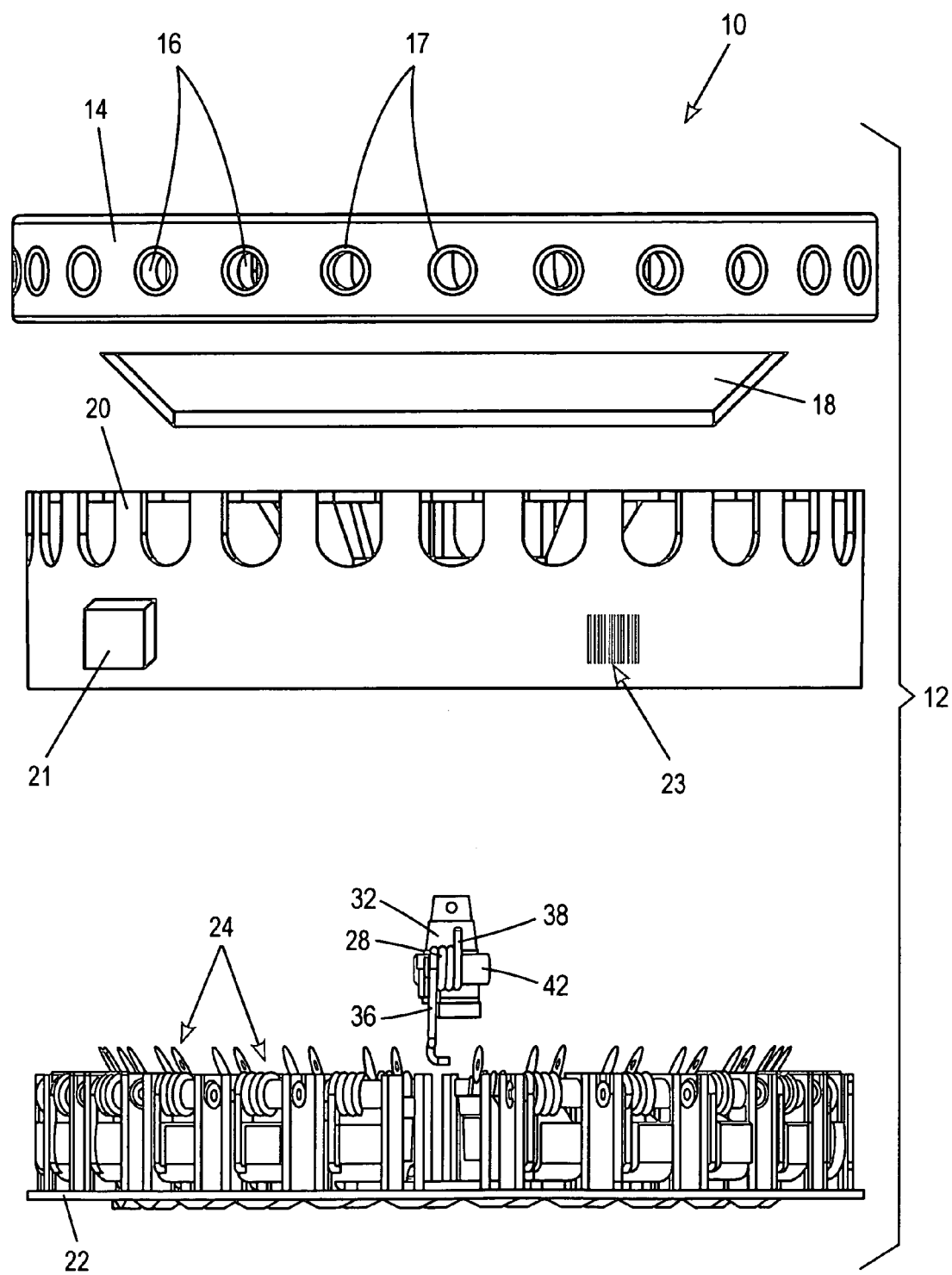
FIG. 3 is an exploded view of the arrangement of FIG. 1.

The housing 12 can be provided in any suitable form. One optional configuration is illustrated in FIGS. 1-3. As illustrated, the housing 12 can comprise a footprint ring 14. The footprint ring 14 comprises a plurality of apertures 16 disposed about its circumference. The footprint ring 14 may optionally comprise a plurality of footprints 17 which surround respective apertures 16 and are attached to the footprint ring 14. Each footprint 17 is configured to be placed on the surface of the skin of a user at a sampling site. The footprints 17 can be annular in shape according to the illustrated embodiment. However, the footprints are not limited to this shape or configuration. Numerous shapes or configurations may satisfy the function of providing a footprint around the site on the surface of the skin from which body fluid is to be expressed, i.e., the sampling site. According to certain embodiments, the footprints 17 are constructed from a material which facilitates the formation of a seal between the skin and the footprints 17. For example, suitable materials for this purpose include a relatively soft elastomeric material, such as a silicone rubber. The footprints 17 can be formed having any appropriate size. For example, the footprints 17 can have a diameter, or opening having a major dimension, of about 3-8 mm. As an alternative to the above described arrangement, a footprint can be provided for the same purpose as part of an integrated meter or device in which the arrangement or cartridge 10 can be placed, as will be described in more detail herein.

According to the illustrated embodiment, the housing 12 further comprises a transparent optical window 18. The transparent optical window 18 can be provided, for example, in order to permit optical communication between a detection device and one or more components located within the arrangement or cartridge 10.

The housing 12 can further include a top cover 20. An inner frame 22 can also be provided. The inner frame 22 may help define a plurality of analysis sites 24 within the cartridge 10.

One beneficial aspect of the arrangement or cartridge 10 of the present invention is that it may be used to carry information which is readable by the device into which it is inserted. Such information can be used to update data and/or code utilized by the device, and can also be used for purposes of accuracy verification and calibration. Various mechanisms can be associated with the cartridge tend to accomplish this purpose, as will be evident to those of ordinary skill in the art. Two exemplary mechanisms are illustrated in FIG. 3. Namely, the cartridge 10 can comprise a mechanism such as a readable memory chip 21 which carries information and/or code which can be read by the device into which the cartridge 10 is inserted. The manner in which the data and/or code is read from the chip 21 can comprise any conventional arrangement for reading the information contained on a memory chip, such as electrical contacts and radio frequency identification/transmission or direct optical communication such as a system of infrared emitters and detector. Another mechanism by which data and/or other information can be provided to the device into which the cartridge 10 is inserted is illustrated in FIG. 3 as comprising a barcode 23, or similar optically-readable mechanism. The barcode 23 is positioned on the exterior of the cartridge such that an optical sensor positioned within the integrated meter can read the information contained in the bars. The optical sensor and a processor within the integrated device can convert the pattern of bars into data as is commonly known in other areas such as point-of-sale scanners. The data read off of the barcode is used to access specific algorithms or lookup tables stored within memory in the integrated meter. This data allows the integrated device to adjust for any variances in the manufacture of the disposable cartridges. A suitable sensor/detector for reading the chip 21 and/or barcode 23 is schematically illustrated as element S/D in FIG. 22.

Figure 4A:
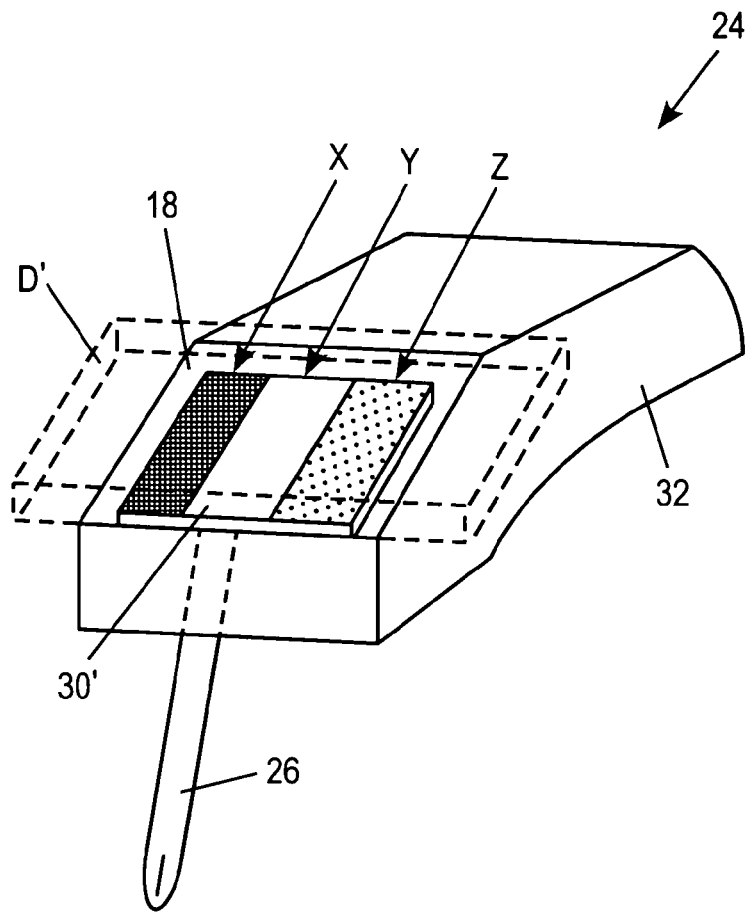
FIGS. 4A-4B are schematic illustrations of a control/calibration mechanism which may be utilized in conjunction with the arrangement of FIG. 1.
Figure 4B:
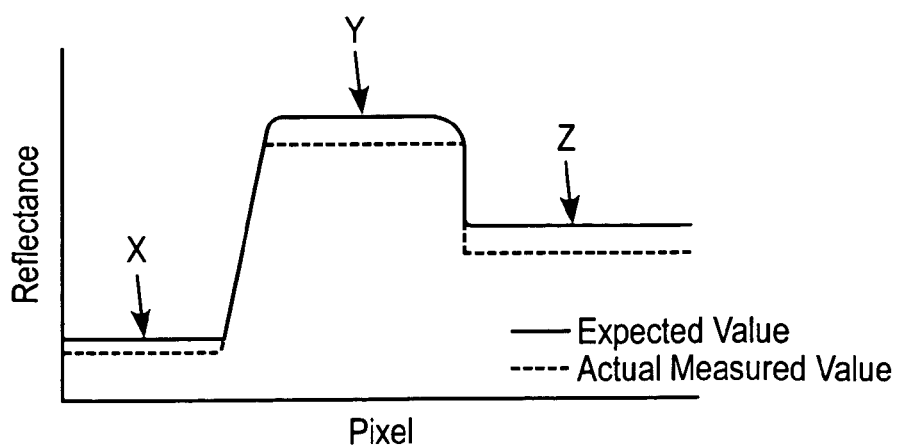

Another beneficial aspect of the arrangement described above is the ability to utilize one or more of the analysis sites 24 for calibration and control purposes. Generally, one or more of the analysis sites 24 can be used to verify the accuracy of test readings and automatically calibrate the system to compensate for any variations which may occur with operation of the device. One such technique and arrangement is illustrated in FIGS. 4A-4B. As illustrated therein, one and possibly more, of the analysis sites 24 are provided with a hub 32 containing a control assay pad 30'. The control assay pad 30' is provided with three distinct regions, each producing known reflectance values. Namely, the first region X having a first darker color, a second uncolored region Y, and a third lightly colored region. As the control assay pad 30' is read by the detector D' through the transparent window 18, the pixels of the detector D' that correspond to each of the regions X, Y and Z produce reflectance readings. This detection is depicted in FIG. 4B. As illustrated therein, the reflectance values actually measured by the detector D' may differ from the known reflectance values of the control assay pad 30'. This difference can be analyzed and compensated for by any suitable technique. For instance, the algorithm utilized to calculate analyte concentration levels can be adjusted to compensate for the difference, thereby leading to more accurate results. Such control and calibration operations can be carried out after each test, or after a number of tests.

As an alternative to the above control assay pad 30', a control fluid can be released into an assay pad and allowed to react with a chemical reagent contained therein. Since the control fluid contains a known concentration of analyte, the measured concentration of analyte can then be compared to the known concentration, and any differences analyzed and compensated for in the manner described above.

Figure 5:
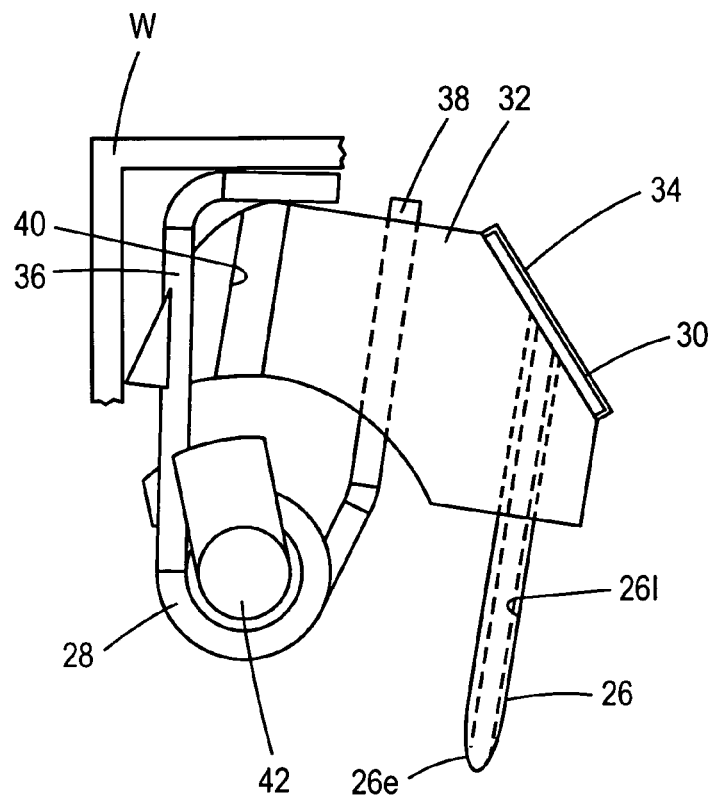
FIG. 5 is a side view of a skin-piercing member, hub and actuator of the arrangement of FIG. 1.

Each sampling and analysis site 24 of the illustrated embodiment comprises a skin penetration member 26. Each skin penetration member 26 can take any suitable form. According to the illustrated embodiment, each skin penetration member 26 is in the form of a hollow needle and has a first in the portion 26e configured to pierce the skin, as well as an inner lumen 26l (FIG. 5). It should be understood that alternative skin penetration members may also be utilized consistent with the principles of the present invention (e.g., solid lancets, etc.). The at least one skin penetration member 26 can take any suitable form. For example, the at least one skin penetration member can comprise a solid lancet or a hollow needle. According to one embodiment, the skin-penetration member 26 is in the form of a so-called "microneedle." As the name implies, microneedles are characterizable by their relatively small outer diameters. For example, a microneedle, as the term is utilized herein, may encompass a skin-penetration member having an outside diameter which is on the order of 40-200 µm. The inside diameter can vary, for example, having an inside diameter on the order of 25-160 µm. Needles are also characterizable in the art by reference to the "gage." By way of illustration, and consistent with the above description, microneedles having a gage ranging from 26-36 are clearly comprehended by the present invention. Certain advantages may be gleaned from the use of such microneedles as the skin-penetration member. In particular, due to their small size, the size of the wound left upon entry into the skin is relatively small, thereby minimizing the pain associated with such needle insertions and allowing for a quicker healing process. However, the present invention is certainly not limited to the use of such microneedles. Thus, for example, according to one possible alternative embodiment, the skin penetration member(s) comprise hollow needles having a gage of about 20-25, or comprising hollow needles having an inner diameter of about 0.007 inches and an outer diameter of about 0.020 inches.

The least one skin-penetration member can be formed of any suitable material, such as metal, plastic, glass, etc.

Each skin-penetration member can be attached to a hub 32. Each hub 32 is, in turn, attached to an actuator 28. It should be understood that a number of different actuators may be utilized according to the principles of the present invention. The actuators can be mechanical, electrical, pneumatic, etc. According to the illustrated embodiment, the actuator 28 is in the form of a torsional spring. Upon activation, the torsional spring drives the hub 32 and the attached skin penetration member 26 through a respective aperture 16 and into the skin of the user. According to certain embodiments, each sampling and analysis site 24 further comprises and analyte quantification member which produces a detectable signal when contacted with a target analyte contained in a sample of body fluid. A number of suitable members are envisioned. The members may be based on conventional technologies such as photometric or electrochemical analysis. According to the illustrated embodiment, an assay pad 30 is provided on each hub 32 which can generally comprises an absorbent material containing a chemical reagent which, upon reaction with a target analyte, produces a chemical reaction that results in a detectable signal. The assay pad 30 is in fluid communication with the inner lumen 22e of the skin piercing element 22. As noted above, the signal can be detected optically, electrochemically, or by other suitable means. According to one embodiment, the assay pad 30, upon reaction with the target analyte, produces a spot which is optically detected by any suitable arrangement or technique. As schematically illustrated, for example, in FIG. 5, the assay pad 30 can be located on an exterior surface of the hub 32 and retained in position by a retaining element or cover 34. The retaining element or cover 34 can take any suitable form, such as a cap that snap fits onto the hub 23, or a strip of adhesive, The retaining element or cover 34 is preferable transparent. Thus, the spot produced on the assay pad 30 by the above-mentioned reaction can be observed optically through the transparent optical window 18 formed along the interior region of the illustrated cartridge housing 12.

Various mechanisms for triggering actuation of a hub 32 and attached skin penetration member 26 will now be described.

Figure 6:
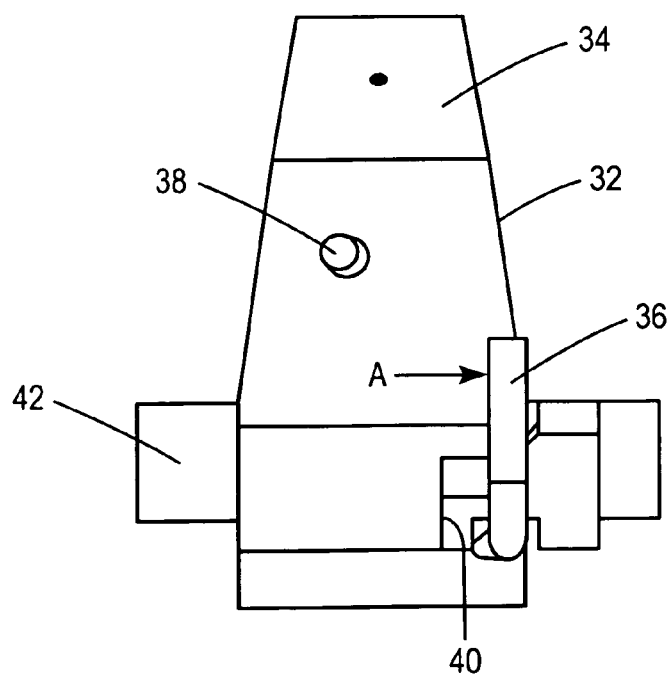
FIG. 6 is a top view of the skin-piercing member, hub and actuator of the arrangement of FIG. 4.

In the exemplary, nonlimiting arrangement illustrated in FIGS. 5-6, the actuator 28 is in the form of the torsional spring having a rear leg 36 and a forward leg 38. The forward leg 38 is fixedly attached to the hub 32 by any suitable means, such as the illustrated bore in the hub 32. The hub 32 is further provided with a mechanism for releasably capturing the rear leg 36 of the torsional spring. According to the illustrated embodiment, the releasably capturing mechanism comprises an open locking groove 40 which is configured to receive the rear leg 36. When the rear leg 36 is disposed within the releasably capturing mechanism, or groove 40, the rear leg 36 and the forward leg 38 are urged toward one another. In this state, the torsional spring has a bias which tends to urge the rear leg 36 and the forward leg 38 apart. Thus, in order to actuate the skin penetration member 26 and the attached hub 32, the rear leg 38 is released from the open locking groove 40 by any suitable mechanism or technique. As illustrated in FIG. 6, the rear leg 36 is urged out of communication with the groove 40 by moving it in the direction indicated by arrow A. The rear leg 36 is prevented from significant movement by virtue of the fact that it is trapped within a wall W of the inner frame, while the forward leg 38 is relatively unrestrained. As a result of the natural bias of the torsion spring urging the rear and forward legs 36, 38 apart, the hub 32 and the attached skin penetration member 26 is urged in an arcing, downward movement such that the skin penetration member 26 passes through a respective aperture 16, and into the surface of the skin of the user. The hub 32 can rotate about the pivot or pin 42 upon actuation.

Figure 7:
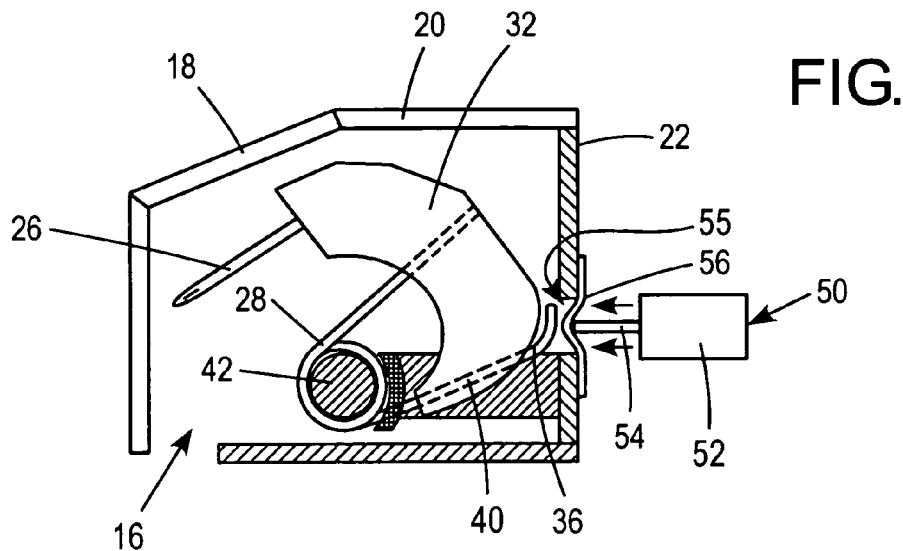
FIG. 7 is a side view of a triggering mechanism for an actuator according to one embodiment of the present invention.

FIGS. 7-10 illustrate further optional aspects of the triggering mechanism constructed according to the principles of the present invention. As illustrated in FIG. 7, the triggering mechanism 50 is provided for the purpose of urging the rear leg 36 of the actuator 28 out of registry with the locking groove 40. According to the illustrative, nonlimiting embodiment, the triggering mechanism 50 comprises a driving portion 52, such as a motor, solenoid, or servo device, and a driven linear actuator arm 54. In order to protect the components contained within the cartridge from environmental contamination, and in order to facilitate the creation of a vacuum pressure at the analysis sites 24, it may be preferable according to certain optional aspects of the present invention to seal each analysis site. While it is noted at the arrangement illustrated in FIG. 7 has an opening 16 corresponding to the aperture contained in the footprint ring 14, this opening will be sealed when the cartridge 10 is applied to the surface of the skin in the manner described above. As illustrated, for example, in FIG. 7, and opening 55 is provided in the frame 22 in order to permit introduction of the linear actuator arm 54. This opening 55 can be sealed by means of a flexible solid membrane 56. The membrane 56 is flexible enough to permit the necessary degree of movement of a linear actuator arm 54 in order to disengage the rear leg 36 of the actuator 28 from the locking groove 40, without being penetrated or broken by this movement.

Figure 8:
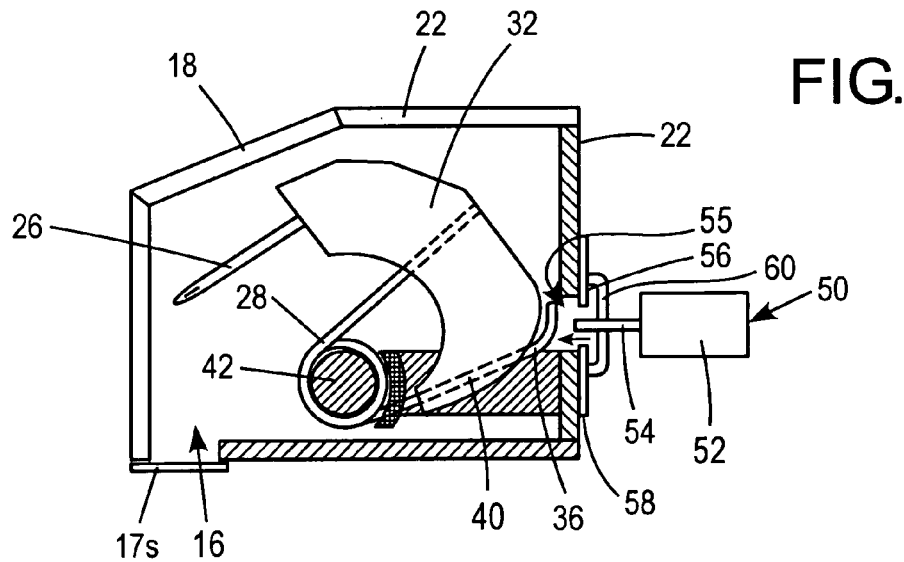
FIG. 8 is a side view of a triggering mechanism for an actuator according to an alternative embodiment of the present invention.

A similar configuration is illustrated in FIG. 8. However, in the embodiment illustrated in FIG. 8, the opening 55 is sealed by the combination of and apertured membrane 58 which has an opening to permit passage of the linear actuator arm 54 therethrough, in combination with a secondary seal 60 which is disposed about the linear actuator arm 54. As illustrated, the secondary sealed 60 is designed to come into firm contact with the apertured membrane 58 upon insertion of the driven linear actuator arm 54 therethrough. Thus, a seal is maintained through this opening 55 in the frame 22 for the purposes described the above. As further illustrated in FIG. 8, the opening(s) 16 in the cartridge may optionally be sealed by any suitable mechanism or member, such as a thin sealing film 17*s*. This seal 17*s* will allow each chamber to remain completely sealed until it is punctured. The seal can either be removed by the user when loading a new disposable or actually punctured by the skin penetration member 26 as it penetrates the user's skin. It should be understood that this aspect of the embodiment illustrated in FIG. 8 can be applied to any of the various embodiments described in this application.

Figure 9:
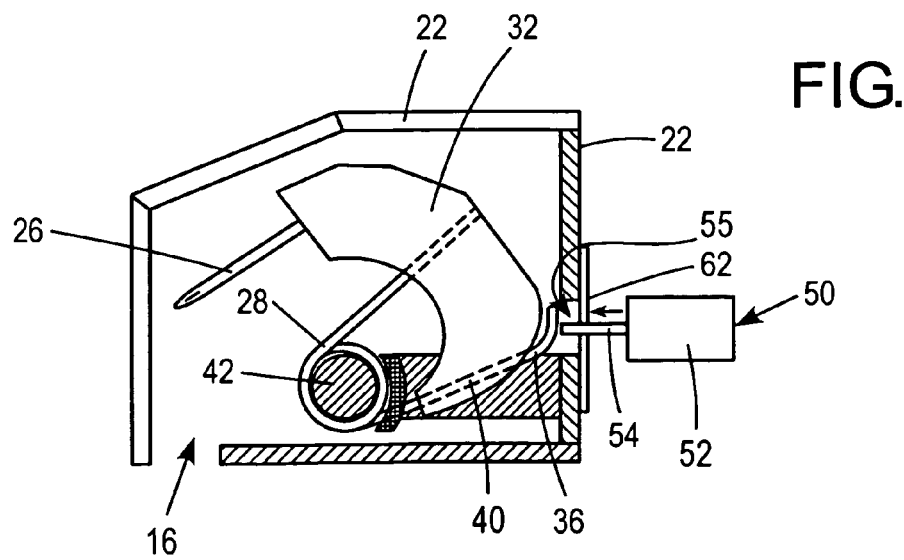
FIG. 9 is a side view of a triggering mechanism for an actuator according to a further embodiment of the present invention.
Figure 10:
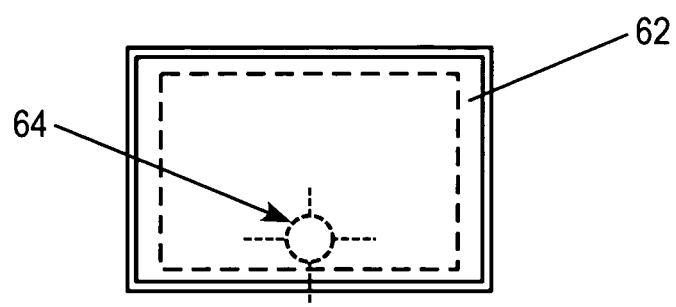
FIG. 10 is a top view of an optional sealing member for the triggering mechanism of FIG. 9 of the present invention.

A further variation of the above arrangements is depicted in FIGS. 9-10. As illustrated therein, the opening 55 in the frame 22 is sealed by means of a piercable membrane seal 62. The piercable membrane seal 62 is normally of a solid construction. However, the piercable membrane seal 62 can be provided with weakened portions or perforations 64 (FIG. 10) which facilitates the creation of an opening therein upon contact with the driven linear actuator arm 54. Upon insertion of the linear actuator arm 54 at the location of the weakened portion or perforations 64, a passageway is formed within the piercable membrane seal 62. However, a relatively tight contact is maintained between the newly formed aperture in the piercable membrane seal 62 and the linear actuator arm 54. This contact serves to maintain at least a significant sealing effect.

Figure 11:
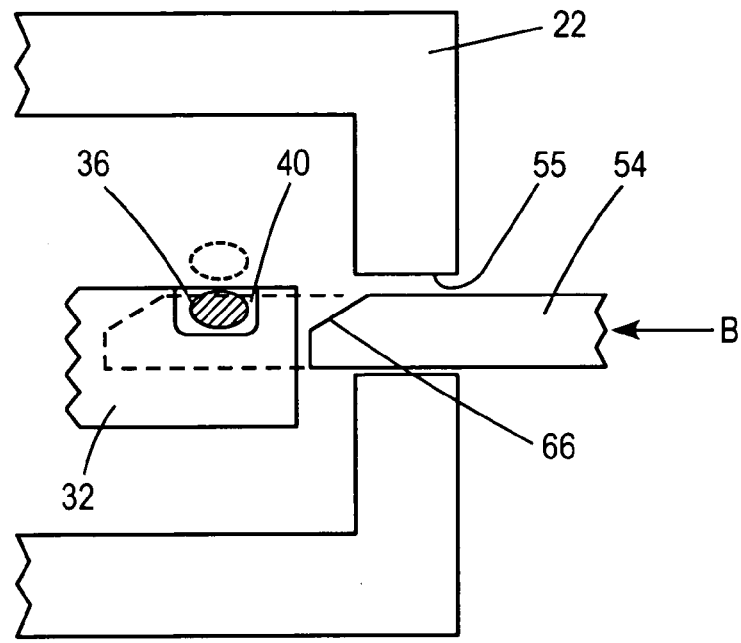
FIG. 11 is a top view of a triggering mechanism according to an optional embodiment of the present invention.

Further alternative embodiments of a triggering mechanism formed according to the principles of present invention are illustrated in FIGS. 11-20. As illustrated in FIG. 11, the linear actuator arm 54 travels through the opening 55 in the direction of arrow B. The opening 55 can be sealed by any suitable mechanism or construction, such as any of the previously described ceiling mechanisms. The arm 54 is provided within angular ramp surface 66 which is designed to interact with the rear leg 36 of the actuator in a manner that pushes it out of engagement with the locking groove 40, as indicated by the relative positions of the linear actuator arm 54 and rear leg 36 shown in broken lines in FIG. 11.

Figure 12:
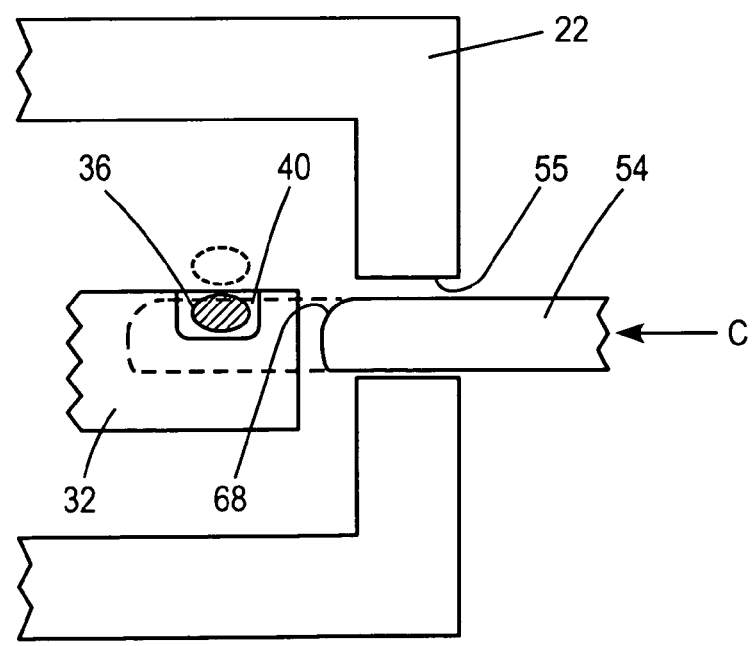
FIG. 12 is a top view of a triggering mechanism according to another embodiment of the present invention.

A further modification of the arrangement of FIG. 10 is illustrated in FIG. 12. According to this modification, the linear actuator arm 54 is provided with a curved or arcuate ramp surface 68 which is also designed to interact with the rear leg 36 of the actuator in a manner which pushes it out of engagement with the locking groove upon traveling a predetermined distance in the direction of arrow C, as indicated by the relative positions of the linear actuator arm 54 and the rear leg 36 shown in broken lines in FIG. 12. Again, the opening 55 can be sealed by any suitable means, such as any of the previously-described sealing constructions.

Figure 13:
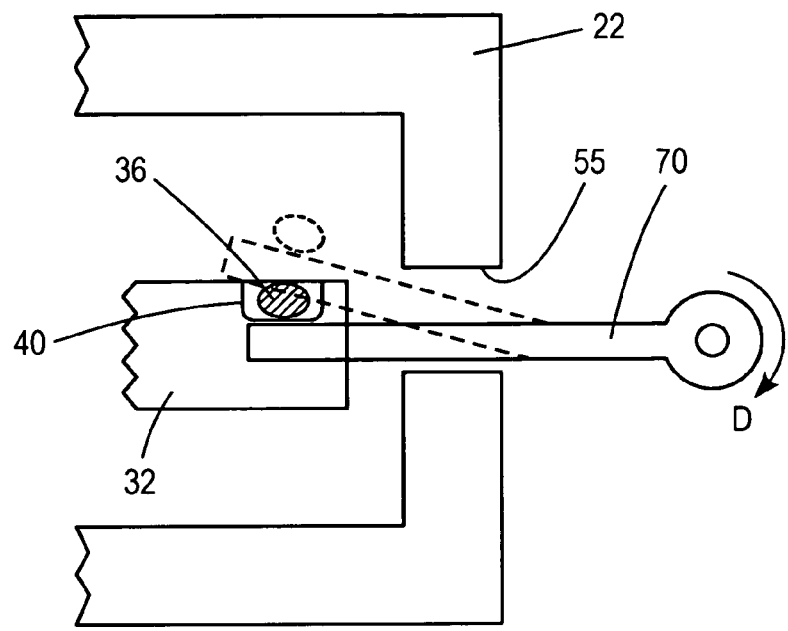
FIG. 13 is a top view of a triggering mechanism according to yet another embodiment of the present invention.

A further embodiment of the triggering mechanism formed according to the present invention is illustrated in FIG. 13. According to this embodiment, a pivotable actuator arm 70 is provided for movement within the opening 55. The opening 55 can be sealed by any suitable mechanism, such as any of the previously described sealing constructions. The pivotable arm 70 is constructed and arranged so as to translate or pivot in the direction indicated by arrow D, thereby forcing the rear leg 36 of the actuator out of communication with the locking groove 40, as indicated in the broken line portion of FIG. 12. The pivotable arm 70 can be driven by any suitable conventional mechanism, such as a motor, solenoid or servo device.

Figure 14:
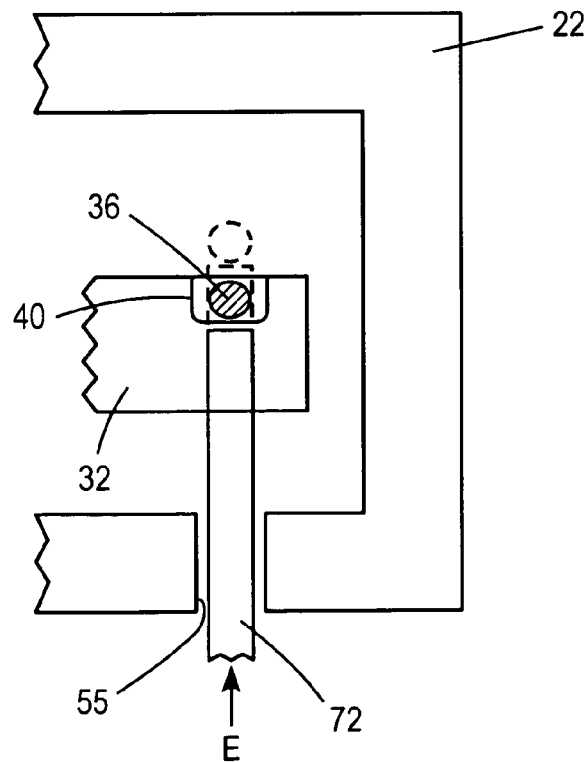
FIG. 14 is a top view of a triggering mechanism according to still another embodiment of the present invention.

A triggering mechanism constructed to still another embodiment of the present invention is illustrated in FIG. 14. According to this embodiment, a linear actuator arm 72 is provided having a construction similar to that of the linear actuator arm 54 described in the previous embodiments. However, the linear actuator arm 72 is oriented at a location which is offset 90° relative to the location of the previously described linear actuator arm 54. As illustrated in FIG. 14, the linear actuator arm 72 is positioned to travel in the direction of arrow E, thereby directly engaging the second end 36 of the actuator at a position adjacent to the bottom of the locking groove 40 and pushing it out of engagement with the locking groove 40, as illustrated by the broken lines in FIG. 14. As with the previously described embodiments, the opening 55 can be sealed by any suitable mechanism, such as any of the previously described sealing arrangements.

Figure 15A:
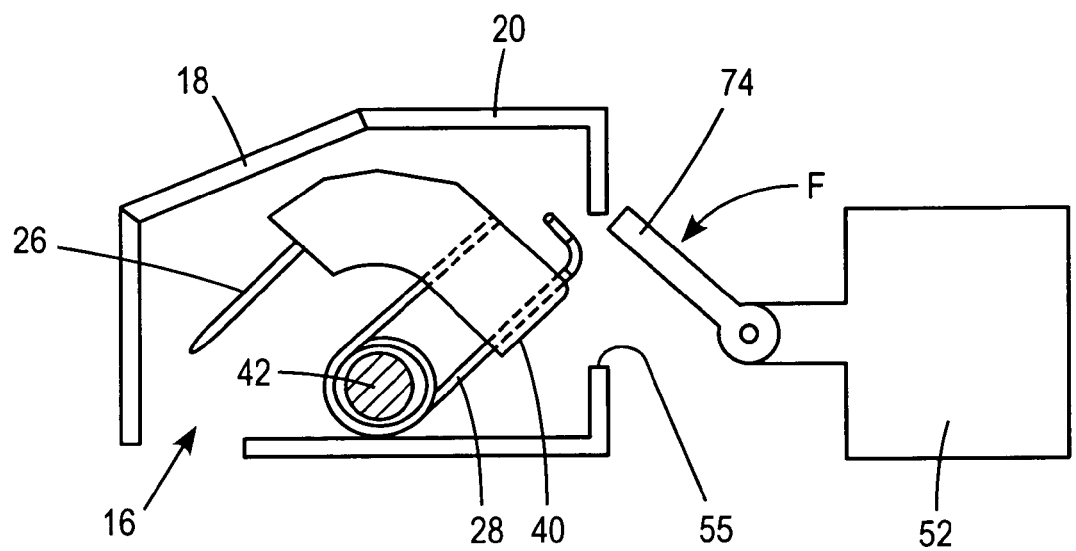
FIGS. 15A and 15B are side and detailed perspective views, respectively, of a further embodiment of a triggering mechanism.
Figure 15B:
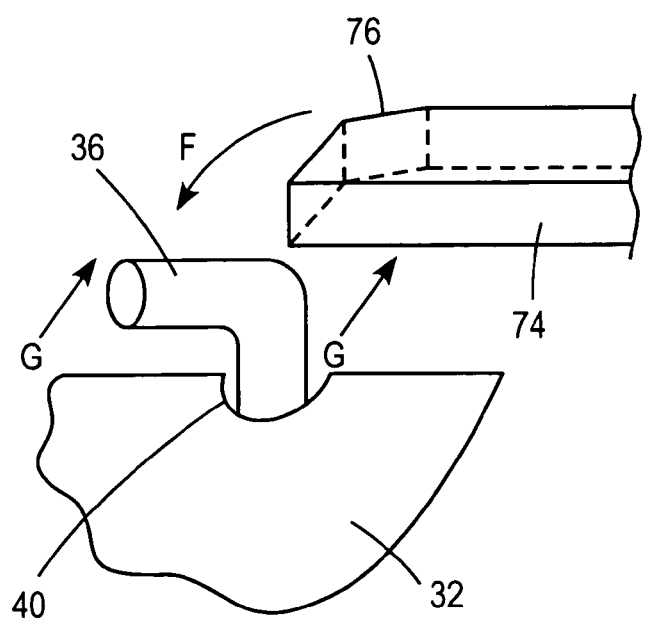
Figure 16:
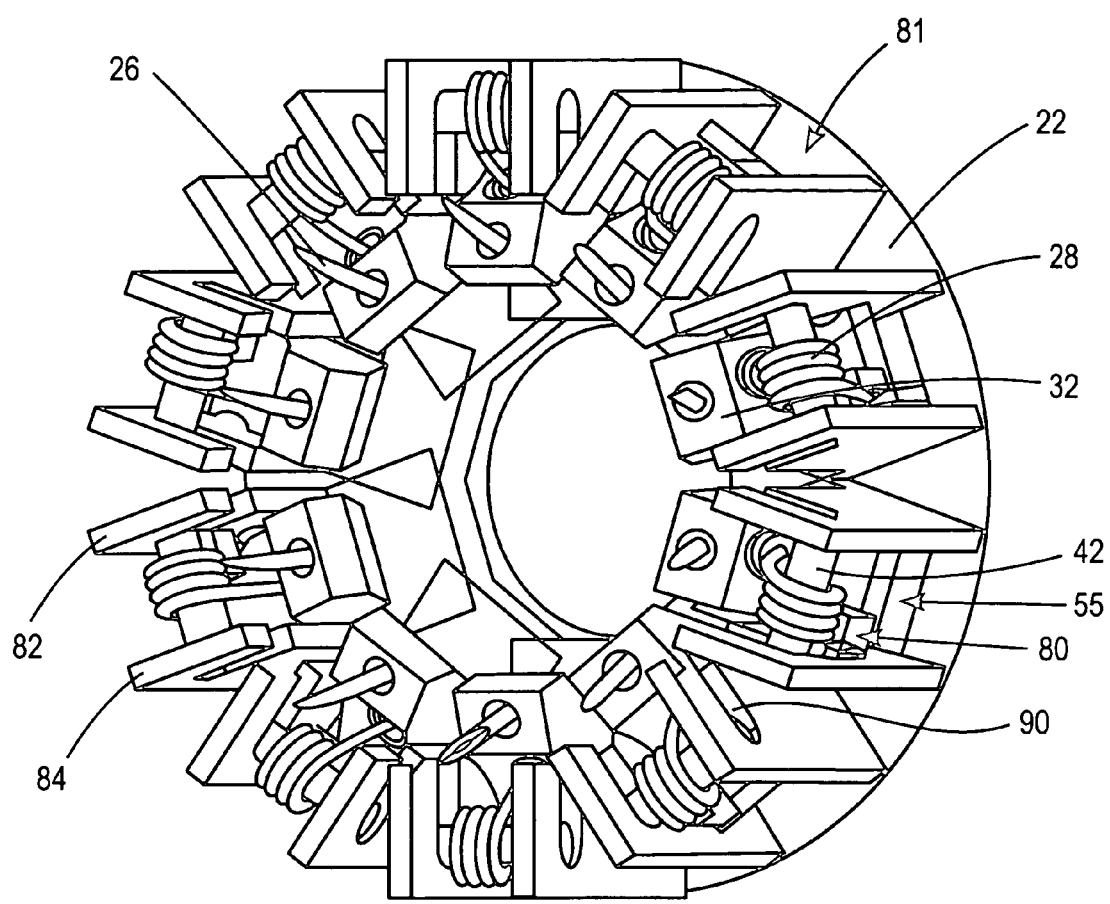
FIG. 16 is a perspective view of a triggering mechanism formed according to a further embodiment of the present invention.
Figure 17:
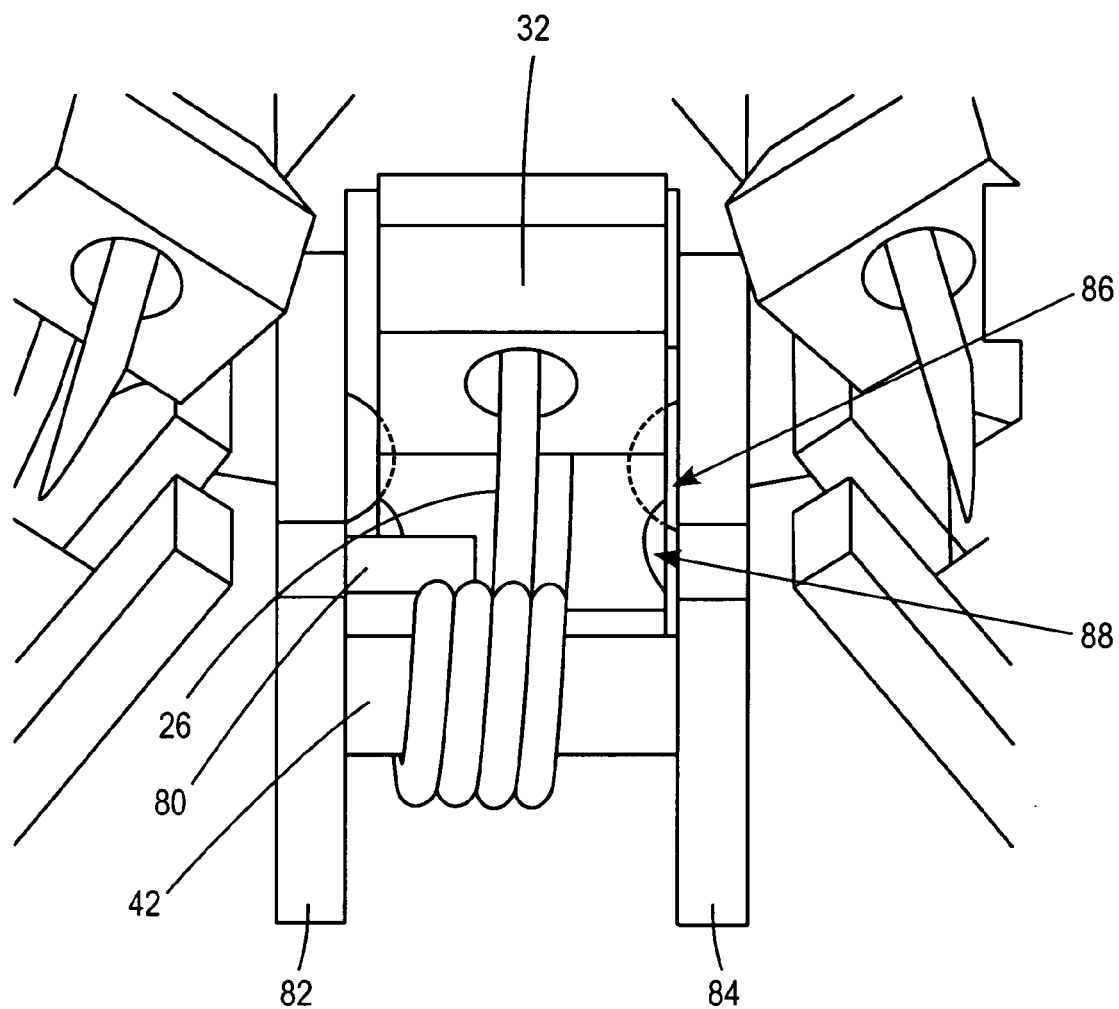
FIG. 17 is a magnified perspective view of a portion of FIG. 16.
Figure 18:
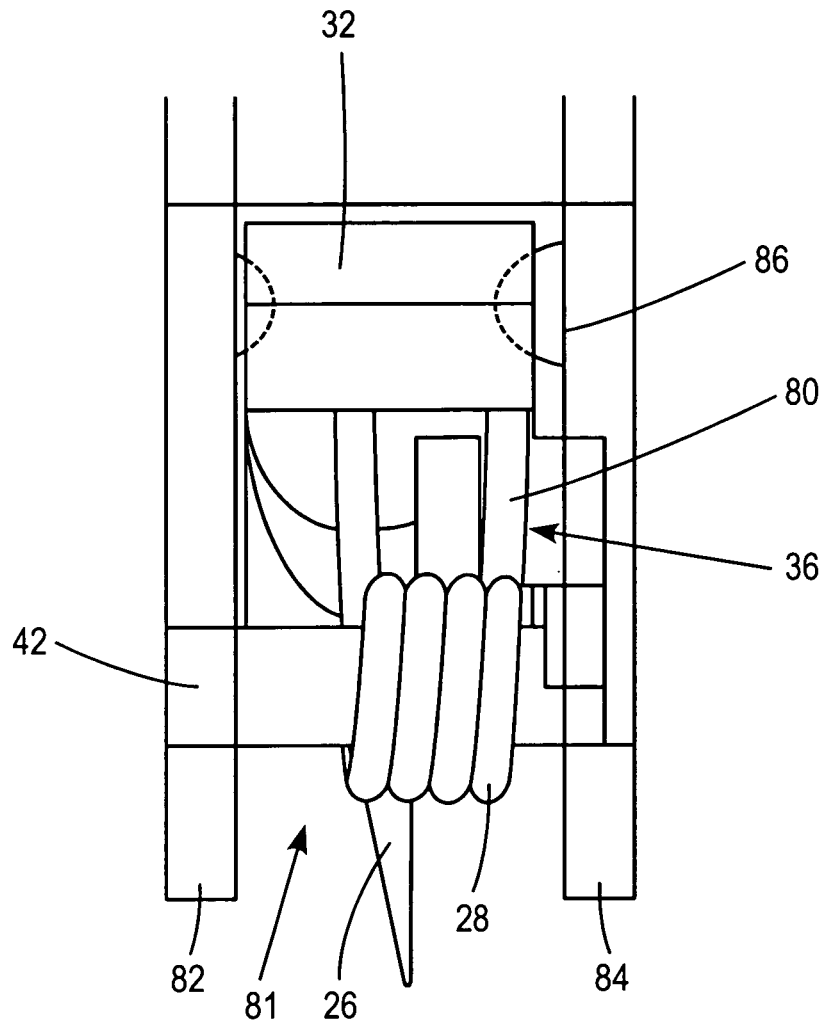
FIG. 18 is a magnified perspective view of a portion of FIG. 16.

As illustrated in FIGS. 15A-15B, a suitable alternative triggering mechanism can be constructed by providing a pivotable actually arm 74 which travels within the opening 55 in the direction indicated by arrow F. The pivotable actuating arm 74 is provided within angular ramp surface 76 which is configured to interact with the rear leg 36 of the actuator upon traveling in the direction indicated by arrow F in a manner which forces the second leg 36 out of communication with locking groove 40 in the direction indicated by arrows G. The opening 55 can be sealed by any suitable mechanism, such as any of the previously described sealing mechanisms.

A further alternative triggering or release mechanism and arrangement formed according to the present invention is illustrated in FIGS. 16-19. According to this embodiment, the rear leg 36 of the actuator 28 is fixedly retained in a locking feature 80 (e.g., FIG. 18) in the pin or pivot 42. The forward leg 38 of the actuator 28 is fixedly retained by the hub 32. The hub 32, actuator 28 and pin or pivot 42 is mounted within a chamber 81 defined by cell walls 82, 84. According to the illustrated embodiment, the pivot or pin 42, and the attached hub 32, actuator 28 is retained between the cell walls 82, 84 via retaining grooves 90 disposed therein. The hub 32 is positioned within the chamber 81 such that the hub is initially locked in a cocked position (e.g., FIGS. 16-17) by interaction between a locking feature associated with the hub 32 and a locking feature associated with the chamber 81. According to the illustrative embodiment, the locking feature associated with the chamber 81 comprises a pair of projections 86, each extending from a respective cell wall 82, 84, and the locking feature associated with the hub 32 comprises a pair of laterally spaced grooves or recesses 88 configured to releasably mate with the projections 86. Numerous modifications to the illustrated locking features are contemplated. For instance, the location of the projections 86 and the grooves 88 can be switched. Additionally, the cooperating projections and grooves can have a multitude of different geometrical configurations.

Figure 19:
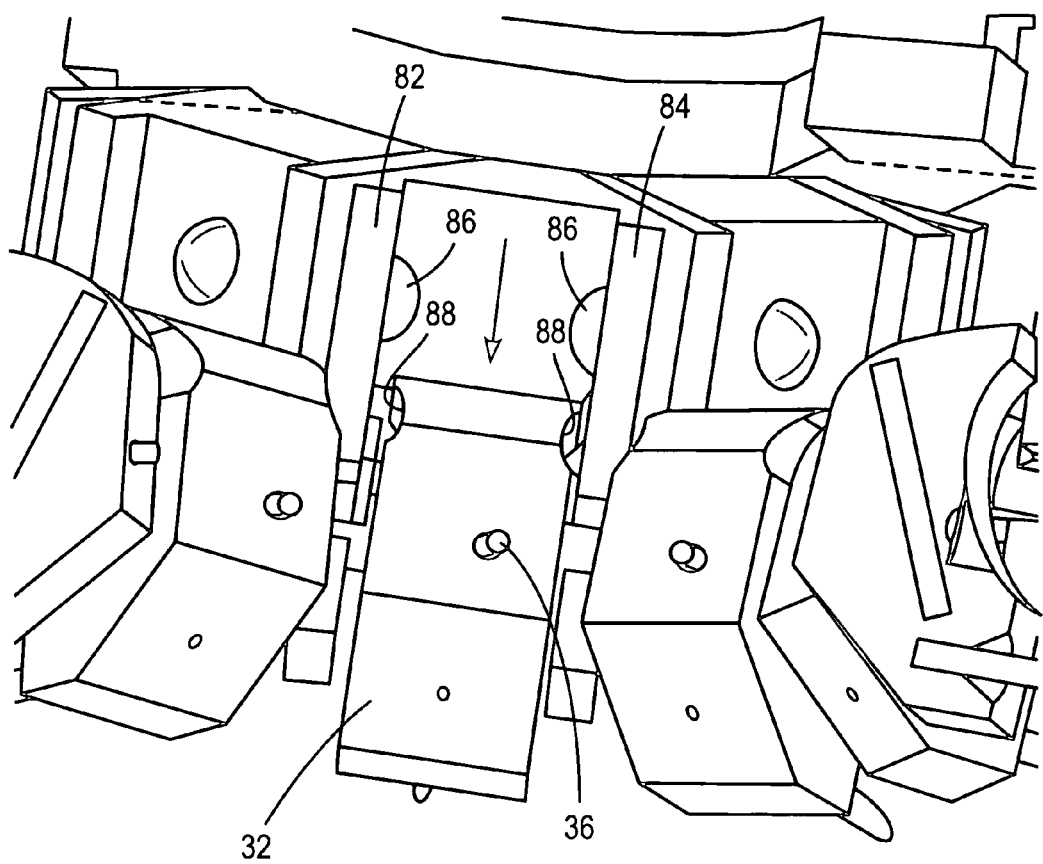
FIG. 19 is a magnified perspective view of a portion of FIG. 16.

When the hub 32 is positioned in the chamber 81 in a locked position, the rear leg 36 and the forward leg 38 are biased away from one another, such that upon disengagement of the locking features 86, 88, (FIG. 19) the hub 32 and the attached skin penetration member 26 is urged and an arcing, downward movement such that the skin penetration member 26 passes into the surface of the skin of the user. The locking features 86, 88 are disengaged by application of a force to the hub 32, as indicated for example by the arrow F (FIG. 19). Any suitable mechanism may be utilized to apply the force necessary to disengage the hub, such as those mechanisms previously described herein.

Figure 20:
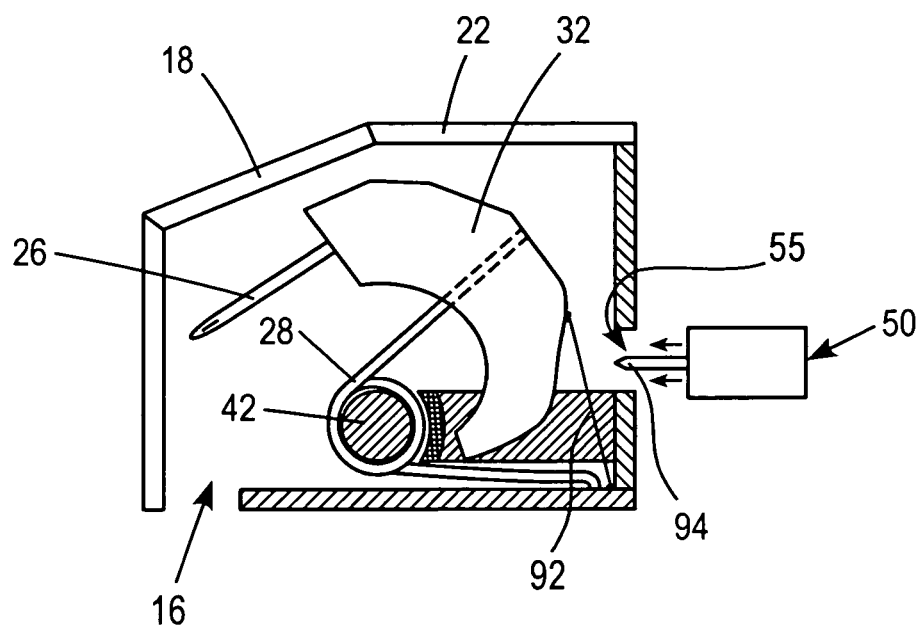
FIG. 20 is a side view of a triggering mechanism for an actuator according to a further alternative embodiment of the present invention.

A further optional triggering mechanism constructed according to the principles of the present invention is illustrated in FIG. 20, the triggering mechanism 50 is provided for the purpose of severing a wire or fuse 92, having one end attached to the hub 32 and the other end attached to a relatively stationary surrounding member. According to the illustrative, nonlimiting embodiment, the triggering mechanism 50 comprises a portion 94 which can comprise at least one of a cutting member or heating element, both capable of severing the restraining wire or fuse 93. The opening 55 can optionally be sealed by means of any of the previously described sealing arrangements.

The arrangement 10 can form at least part of a device which functions only to sample body fluid. For example, the arrangement 10 can be used to express body fluid in the form of a drop of blood which pools on the surface of the skin of the user. This drop of blood can then be transferred to another separate device which then transports and/or analyzes the sample for a target analyte. Alternatively, the arrangement 10 may express a sample of body fluid from the digit D, and then transport the sample to a location which can then be accessed for further analysis by a separate device. For instance, the sample body fluid can be transported to a reagent-containing pad, also contained within the arrangement 10. The sample then reacts with the reagent to produce a detectable spot or signal. The reagent pad can then be analyzed by a separate meter using photochemical, electrochemical, or other suitable techniques known per se to those skilled in the art. The reagent pad can remain within the arrangement 10 during the aforementioned analysis. Alternatively, the reagent pad can be removed from the arrangement 10 and inserted into a separate device, such as an electrochemical or photometric meter.

According to a further aspect of the present invention, the above-described arrangements and techniques as previously described herein, can form at least part of an integrated device. As previously noted, as used herein, the term "integrated device" or "integrated meter" means a device or meter that includes all components necessary to perform sampling of the body fluid, transport of the body fluid, quantification of an analyte, and display of the amount of analyte contained in the sample body fluid. Thus, according to the principles of the present invention, an integrated device or meter can comprise one or more, or any combination, of the features previously described herein. According to further aspects of the present invention, and integrated meter or device can comprise additional components and/or features, which are described as follows.

It should be understood that while not required, any of the above-described triggering mechanisms can form part of a separate sampling only device or part of an integrated device into which the cartridge 10 is placed.

Figure 21:
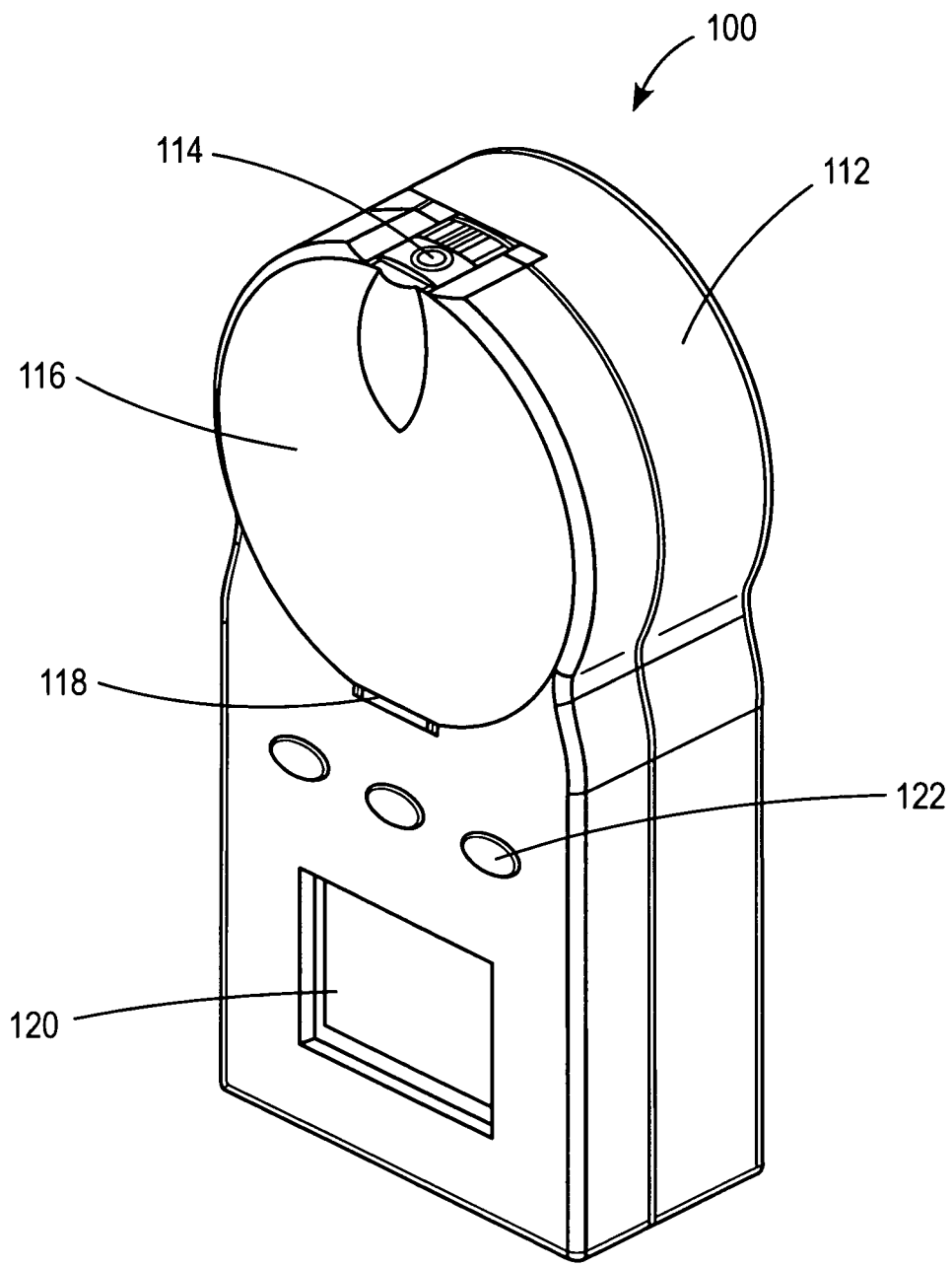
FIG. 21 is a perspective view of an integrated meter or device which can incorporate arrangements formed according to the present invention.
Figure 22:
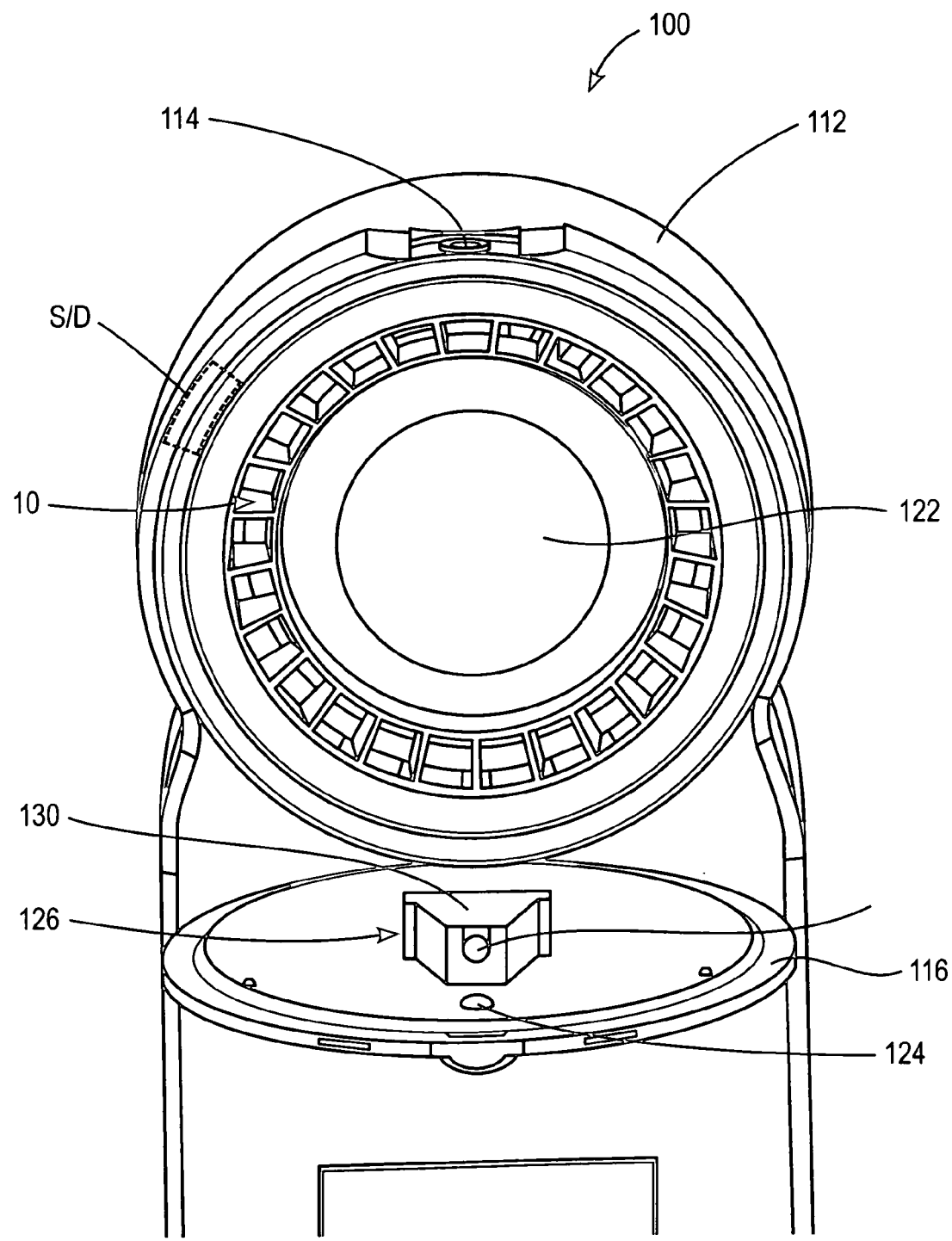
FIG. 22 is a perspective view of certain details of the integrated meter or device of FIG. 21.
Figure 23:
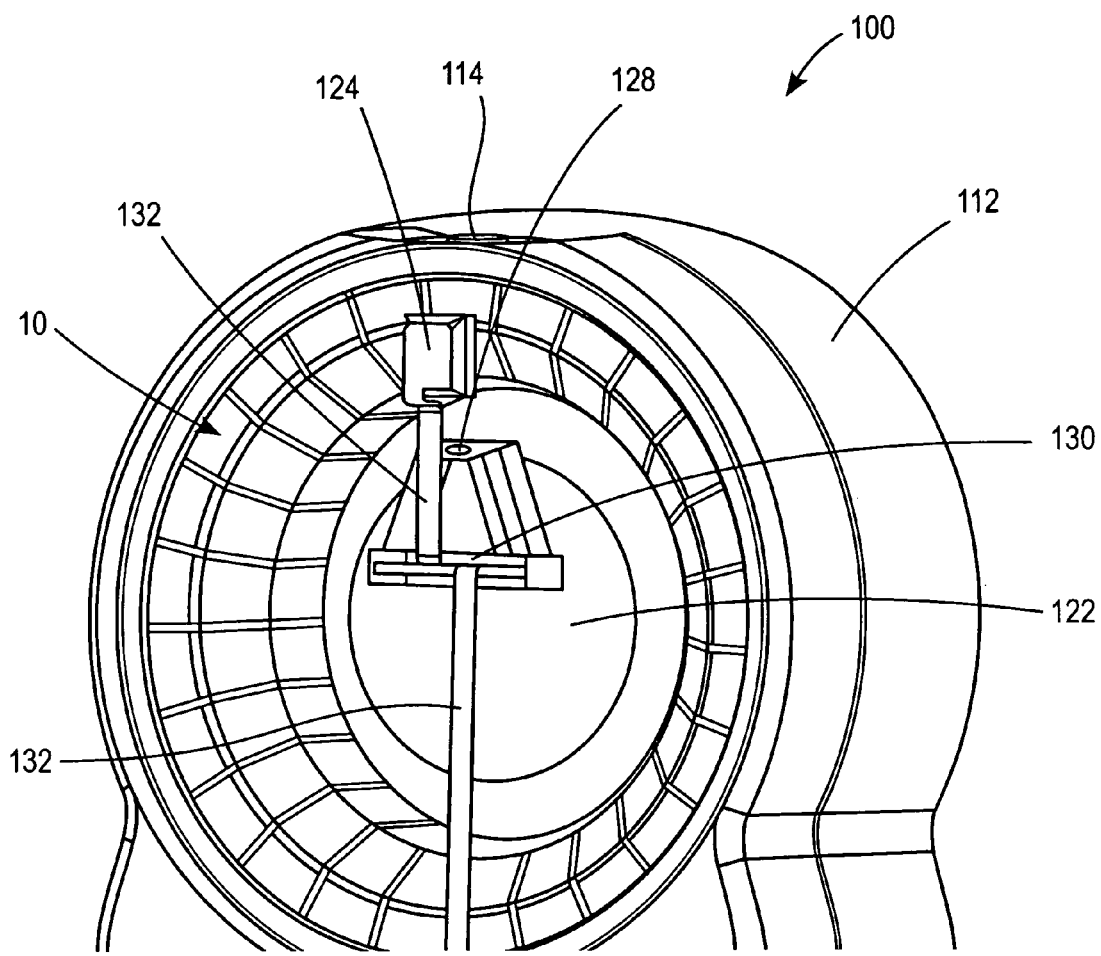
FIG. 23 is a perspective view with parts of the integrated meter or device shown in transparency to reveal certain details contained therein.

One such integrated meter is illustrated FIGS. 21-23. As illustrated therein, the integrated meter 100 generally comprises a housing 112. The integrated meter 100 may further comprise a footprint 114 of the type previously described. A door 116 can be provided on the housing 112. The door 116 is connected via a hinge 118 to the housing 112. As illustrated in FIGS. 22-23, the door 116 can be opened to reveal a cartridge 10 containing a plurality of skin-piercing elements and analysis sites, as previously described herein. In the illustrated embodiment, the integrated meter 100 further includes a display 120 for communicating the results of the analysis on the sample body fluid for the presence and/or concentration of an analyte contained therein. The integrated meter 100 may further include one or more buttons 122 which can be pressed by the user to engage various functions and interfaces of the integrated meter 100.

FIG. 22 is an illustration of the integrated meter 100 with the door 116 opened to reveal further details of the interior components of the integrated meter 100. As illustrated therein, the housing 112 contains a cartridge 10 therein. In the illustrated embodiment, the cartridge 10 is circular and contains a plurality of skin-piercing elements and analysis sites. The cartridge 10 is mounted about a central hub 122 and is rotatable thereon. Thus, upon sampling a skin-piercing element is driven through an opening in the housing in registry with the footprint 114 and pierces the skin of the user. Once the test has been completed, the cartridge 10 can be rotated such that an unused skin-piercing element now comes into registry with the opening in the housing and the corresponding opening in the footprint 114 in preparation for the next sampling event. It should be understood that the present invention is not limited to the illustrated circular cartridge having the particular configuration depicted in the drawing figures. To the contrary, a number of alternative cartridge configurations are possible, such as a slidable linear or polygonal configuration (not shown). Also illustrated in FIG. 22 is the presence of a light source 124 disposed on the back of the door 116. The light source 124 can take any suitable form, such as a light emitting diode. It should be understood that alternative light sources may also be utilized. The function of the light source 124 will be described in further detail below.

In this regard, light emitted from the light source 124 is incident upon an assay pad (e.g., 30), and reflects off the surface thereof. Upon formation of a reaction spot on the surface of the assay pad, the amount of light reflected off the reaction spot differs from the light reflected off of other portions of the reagent pad containing no such reaction spot. This reflected light is picked up by the detector 126. The detector 126 may comprise a lens 128 and optical detector element 130.

The optical detector element 130 generally comprises one or more detector elements. According to one alternative construction, the detector element 130 comprises a plurality of detector elements formed in an array. The array can take any suitable configuration, and can be a linear array according to one nonlimiting example. The detector elements can comprise any suitable construction. For example, the detector elements 130 can comprise a photo diode, CCD, or CMOS based detector element. The signals transmitted to the detector element 130 are passed on to suitable electronics contained within the housing 112 via suitable electrical connectors, such as flexible ribbons 131 (FIG. 23). The specifics of the electronics and signal interpretation being familiar to those of ordinary skill in the art. While not necessary to enable practice of the presently claimed invention, further details concerning the construction, function and arrangement of the analysis sites, and components contained therein, can be gleaned from the disclosure contained in U.S. Patent Application Ser. No. 60/721,966, entitled DEVICE FOR FLUID ANALYSIS WITH SAMPLE EXTRACTION AND TRANSPORT, the entire content of which is incorporated herein by reference. Similarly, while not necessary to enable practice of the presently claimed invention, further details concerning the structure, function, and arrangement of the detector 126, and the components contained therein, can be gleaned from the disclosure contained in U.S. patent application Ser. No. 11/239,122, entitled ANALYTE DETECTION DEVICES AND METHODS WITH HEMATOCRIT/VOLUME CORRECTION AND FEEDBACK CONTROL, the entire content of which is incorporated herein by reference.

An integrated meter incorporating an arrangement formed according to the present invention can be configured for digital body fluid sampling and analysis as well as alternate-site body fluid sampling and analysis, which may be performed at either location at the election of the user.

Figure 24:
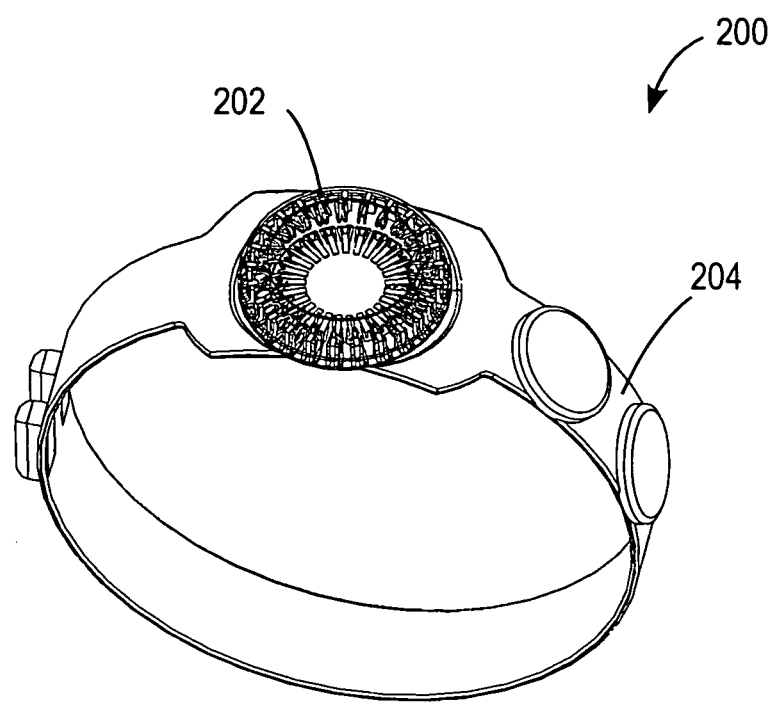
FIG. 24 is a perspective view of an alternative embodiment of an integrated device which may include arrangements formed according to the present invention.

As evident from FIGS. 21-23, the integrated meter 100 is configured for handheld use. However, the invention is not limited to handheld devices. For example, the present invention is also directed to integrated meters that are wearable. An example of such a wearable device is illustrated in FIG. 24. The wearable integrated device 200 illustrated therein can be generally composed of a functional portion 202 and a body-attachment portion 204. The functional portion can comprise an arrangement 10 of the type described herein. The functional portion can also have one or more of the features and elements of the handheld integrated meter described above.

As previously noted, according to certain embodiments of the present invention, the concentration of an analyte contained in a sample of body fluid can be measured using a photometric technique wherein the assay pad is interrogated with a light source and a detector thereby producing a signal indicative of a color change caused by reaction between an analyte and reagent contained in the assay pad, which is then correlated to the concentration of analyte contained in the sample.

The present invention provides photometric analysis devices, arrangements and techniques that facilitate their incorporation into devices and arrangements of the type described above that are compact, discrete, wearable or handheld, and capable of performing multiple tests without reloading testing components.

Figure 25:
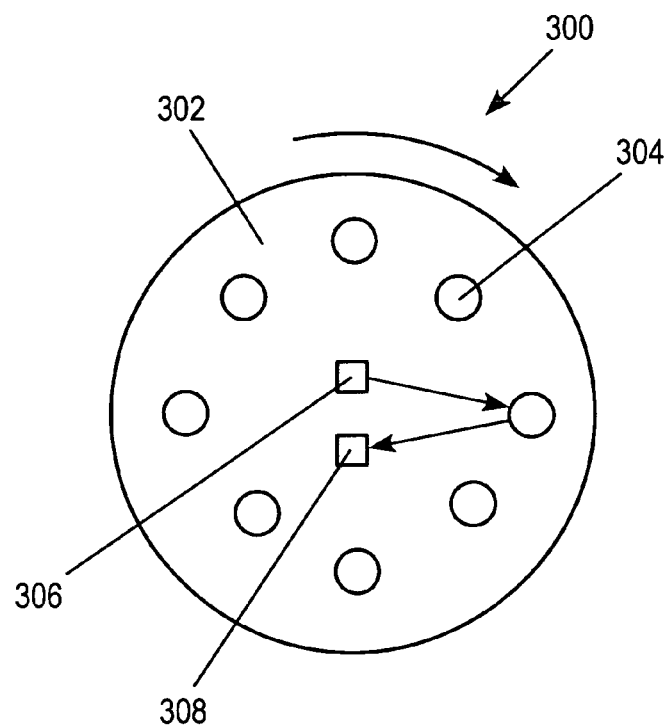
FIG. 25 is a schematic illustration of an optical detection arrangement formed according to one embodiment of the present invention.

According to a first embodiment, a photometric analysis arrangement constructed to satisfy at least the above-noted objectives is illustrated in FIG. 25. As illustrated therein, the arrangement 300 generally comprises a platform or stage 302, a plurality of assay pads 304 containing chemical reagents, a single light source 306, and a single detector 308. The light source 306 may be provided by any suitable device, such as a light emitting diode (LED), similarly, the detector may comprise any suitable device, such as one or more CMOS, CCD, photodiode or infrared detector elements. According to one embodiment, the detector 308 comprises an array of CMOS detector elements.

According to the arrangement 300, the plurality of assay pads 304 are provided at fixed locations relative to the platform or stage 302. Thus, no relative movement between the assay pads 304 and the platform 302 is possible. The light source 306 and the detector 308 are also provided at fixed locations independent of the platform or stage 302. The light source 306 is arranged to direct light toward a specific assay pad 304 when brought into registry therewith. Similarly, the detector 308 is arranged to receive light reflected off the assay pad that is positioned at a predetermined location. The platform 302 is rotatable, as indicated by the arrow contained in FIG. 25, such that each of the plurality of assay pads 304 may be indexed and brought into registry with light source 306 and the detector 308 for analysis.

Figure 26:
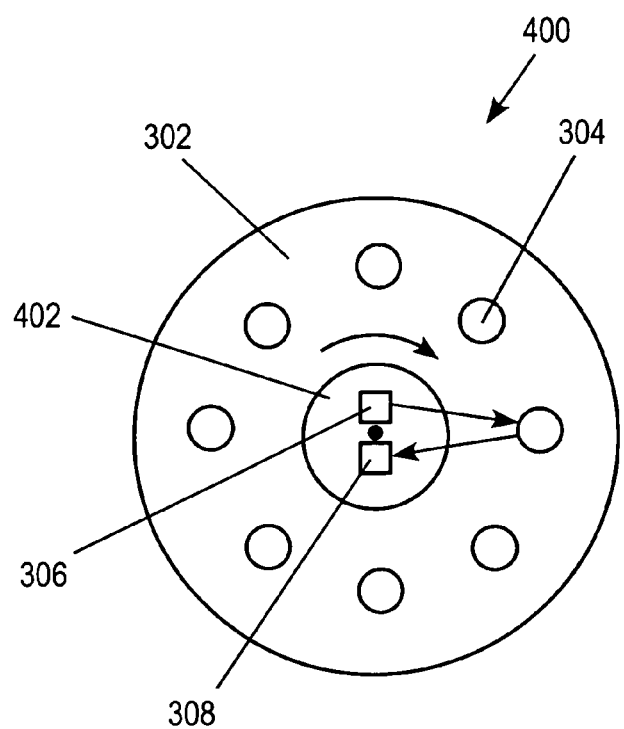
FIG. 26 is a schematic illustration of an optical detection arrangement formed according to an alternative embodiment of the present invention.

A variation of the arrangement 300 is depicted in FIG. 26. The arrangement 400 is constructed in a manner that shares many of the same features previously described in connection with the arrangement 300. According to the arrangement 400, platform 302 is fixed and is not rotatable. Both the light source 306 and the detector 308 are mounted on a second platform or stage 402. Both the light source 306 and the detector 308 are provided at fixed locations relative to the platform 402, such that relative movement therewith is not permitted. According to the arrangement 400, each of the individual assay pads 304 are indexed, or brought into registry the light source 306 and the detector 308 by rotating the second platform 402 in the manner indicated by the arrow appearing in FIG. 26.

Figure 27:
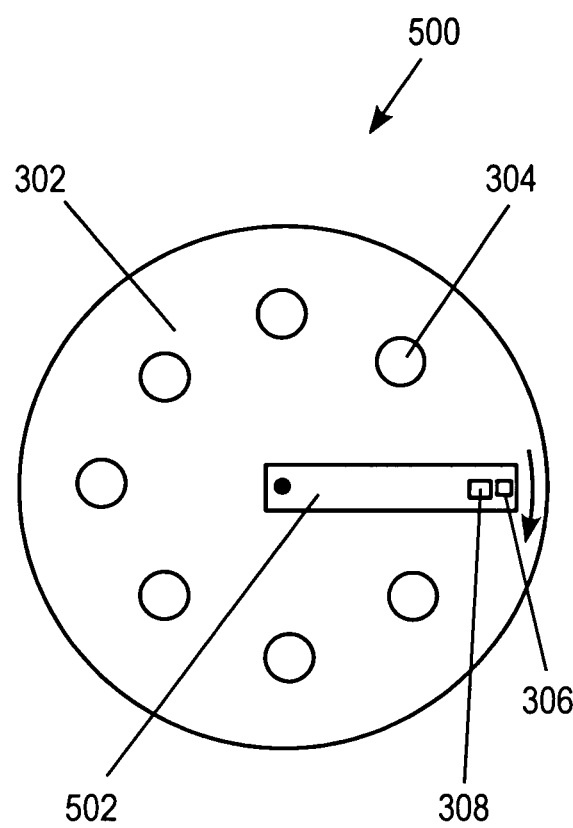
FIG. 27 is a schematic illustration of an optical detection arrangement formed according to a further alternative embodiment of the present invention.

A further optional modification of the arrangements 300, 400 is depicted in FIG. 27. According to the arrangement 500, the platform 302 is fixed, and is not movable. Both the light source 306 and the detector 308 are mounted on an indexing arm 502 in a fixed manner. According the arrangement 500, the light source 306 and the detector 308 are indexed, or brought into registry with each of the assay pads 304 by rotating the movable indexing arm 502 in the manner indicated by the arrow appearing in FIG. 27. Thus, the light source 306 and the detector 308 are brought to a position which is located above a selected assay pad 304. According to this arrangement 500, light is emitted downwardly from the light source 306 toward the assay pad 308. At least a portion of this light is then reflected off the assay pad 304 in a generally upward direction such that it is then received by the detector 308.

Figure 28:
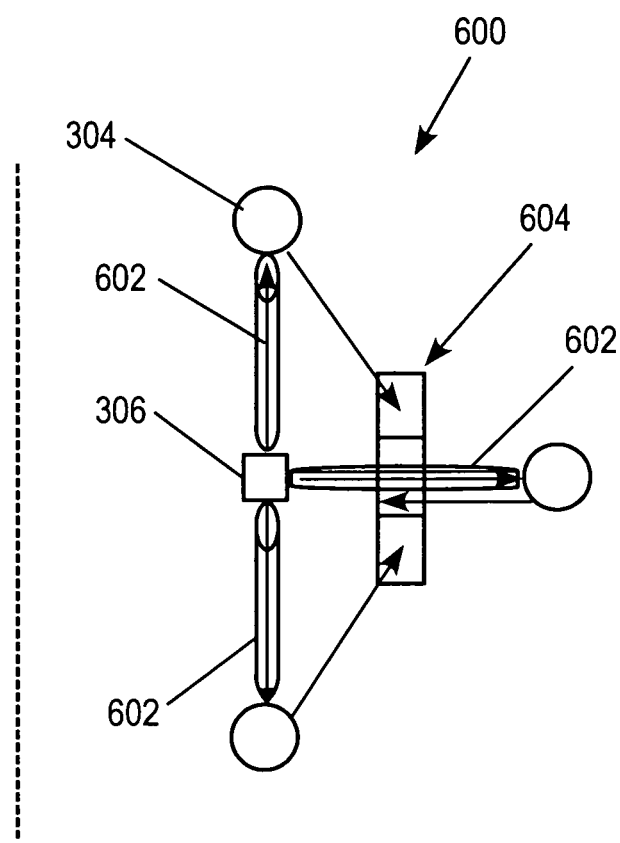
FIG. 28 is a schematic illustration of an optical detection arrangement formed according to another embodiment of the present invention.

In certain instances, it may be advantageous to eliminate the need to move the assay pads 304 relative to the light source 306 and the detector 308 in order to selectively index or bring the components into registry therewith for analysis. Once such arrangement which accomplishes this objective is illustrated in FIG. 28. According to the arrangement 600, each of a plurality of assay pads 304 may be individually interrogated without the necessity of providing relatively movable components within the system. According to illustrated arrangement 600, a plurality of light pipes or similar light transmitting elements 602 are provided which communicate between a single stationary light source 306 and each of a plurality of assay pads 304. The detector 604 is positioned such that it may receive light reflected light off of each individual assay pads 304. In order to accomplish this objective, the detector 604 may be partitioned, or formed as an array of discrete detector elements, as illustrated in FIG. 28. Thus, the detector 604 comprises a plurality of sections, each of which is committed to receive light reflected off of a selected assay pad 304. The light emitted from the light source 306 may be multiplexed or selectively transmitted to a particular assay pad 304. This multiplexing can be accomplished by any suitable technique familiar to those in the art.

Figure 29:
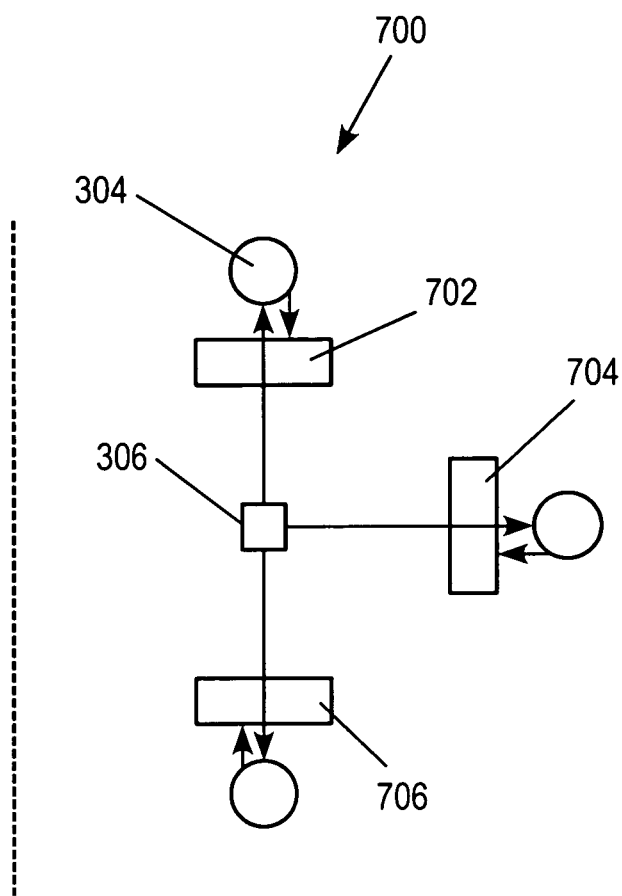
FIG. 29 is a schematic illustration of an optical detection arrangement formed according to still another embodiment of the present invention.

One possible variation of the arrangement 110 is depicted in FIG. 29. According the arrangement 700, like the arrangement 600, a plurality of analysis sites may be interrogated without the use of relatively movable components. According to the arrangement 700, a single light source 306 is provided which transmits light to all of the assay pads 304 simultaneously. A plurality of detector elements 702, 704, 706 are provided, each of which is positioned in registry with light reflected off of a respective assay pad 304. Each of the individual detector elements 702, 704, 706 may be multiplexed, or selectively activated in order to read only the desired assay pad 304. This multiplexing may be accomplished by any suitable means, as familiar to those in the art.

An exemplary body fluid sampling and analysis methodology or technique, which may be utilized in conjunction with any of the above-mentioned arrangements, devices or integrated meters, but is not necessarily limited thereto, is described as follows.

A user loads a fresh disposable cartridge containing a plurality of skin penetration members and analysis sites into an integrated meter. The integrated meter then reads calibration data contained in or on the cartridge. This data can be read in any suitable manner. For example, a bar code may be placed on the cartridge which can be optically read by the optical assembly contained within the meter. Alternatively, the data is contained on a chip carried by the cartridge that is read upon insertion into the integrated meter. The integrated meter then selects the proper lookup table or algorithm to calculate an aggregate glucose measurement taking into consideration the calibration data. The meter may then place itself in a ready mode waiting for a trigger to initiate sampling and testing. The user then either manually presses a button or trigger to initiate sampling and analysis, or the device verifies that it is properly positioned on the skin of the user and ready to begin the sampling and analysis procedure. Suitable sensors to accomplish this include optical, capacitive or pressure sensors. The device may then initiate a catalyst which acts to facilitate the expression of body fluid. According to one alternative embodiment, the catalyst is an inflatable member that exerts pressure on a digit. Alternatively, the catalyst is vacuum pressure which generates suction at the sampling site. Sensors present in the meter may be used to monitor and control the positive or negative pressure of the catalyst. After achieving a target pressure for a desired period of time, the skin penetration member (e.g., a hollow needle) is actuated and driven into the skin of the user to create a wound site. The skin penetration member comes to rest in or directly on the wound created at the sampling site where it is in the desired position for collecting a sample of body fluid expressed from the wound. The integrated meter may further include a mechanism for detecting a whether a sufficient amount of sample has been expressed. Details of such suitable detection techniques are described in detail in U.S. Pat. No. 7,052,652, entitled ANALYTE CONCENTRATION DETECTION DEVICES AND METHODS, the entire content of which is incorporated herein by reference. Once the desired amount of body fluid has been obtained, the catalyst is deactivated. A sample of body fluid is in fluid communication with a device or mechanism which creates a detectable signal upon reaction within analyte present in the sample body fluid. For example, one such suitable mechanism is an absorbent pad containing a chemical reagent which, upon reaction with the analyte produces a reaction spot which can be optically detected. An optical assembly which is an optical communication with the above described signal generating mechanism is utilized to detect the signal created via reaction with the analyte and communicate the signals to supporting electronics contained within the meter. The concentration of a target analyte (e.g., glucose) can then be calculated using these signals as a basis. Additional factors may be considered during these calculations, such as the sample size, levels of other substances contained in the sample (e.g. hematocrit), etc. Such optional calculation techniques are described in further detail in U.S. patent application Ser. No. 11/239,122, entitled ANALYTE DETECTION DEVICES AND METHODS WITH HEMATOCRIT/VOLUME CORRECTION AND FEEDBACK CONTROL, the entire content of which is incorporated herein by reference. These calculations quantify the amount of analyte contained in the sample body fluid. This quantity is displayed on a suitable display contained within the meter which can be easily read by the user. The integrated meter then automatically indexes the disposable cartridge to present a fresh unused skin penetration member which will be utilized to perform the next sampling and analysis event.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. §112, ¶6, unless the term "means" is explicitly used.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. An arrangement comprising:
   a housing;
   a plurality of sampling and analysis sites contained within the housing, each of the sampling and analysis sites comprising:
   a skin-penetration member having a first end configured to pierce skin, and an inner lumen in communication with the first end;
   a spring actuator configured to drive the skin-penetration member into skin of a user;
   a hub, wherein the skin-penetration member and the spring actuator are attached to the hub;
   a pin, wherein the hub is configured to rotate around the pin; and
   an analyte quantification member disposed on or within the hub, wherein the analyte quantification member is in fluid communication with the inner lumen of the skin-penetration member.

2. The arrangement of claim 1, wherein the housing further comprises a plurality of footprints, wherein each footprint surrounds a respective aperture and is configured to be applied to a sampling site on the skin of the user, and wherein the spring actuator of at least one of the plurality of sampling and analysis sites is configured to drive the skin-penetration member of the same sampling and analysis site through at least one of the respective apertures.

3. The arrangement of claim 2, wherein each footprint has an opening, the opening having a diameter or major dimension of 3-8 mm.

4. The arrangement of claim 2, wherein each footprint comprises an elastomeric seal.

5. The arrangement of claim 1, wherein at least a portion of the housing is transparent and provides optical communication with each analyte quantification member.

6. The arrangement of claim 1, wherein the skin-penetration member of at least one of the sampling and analysis sites comprises a microneedle.

7. The arrangement of claim 1, wherein the spring actuator of at least one of the sampling and analysis sites comprises a torsional spring configured to urge the skin-penetration member along an arcuate path.

8. The arrangement of claim 7, wherein the skin penetration member of the at least one sampling and analysis site that comprises a torsional spring is configured to obstruct a wound opening in the skin of the user after the torsional spring moves from a compressed position to a relaxed position.

9. The arrangement of claim 7, wherein at least one of the sampling and analysis sites that comprises a torsional spring lacks a positive stop to limit the penetration depth of the skin-penetration member of the respective sampling and analysis site.

10. The arrangement of claim 1, wherein the hub of at least one of the sampling and analysis sites comprises at least one of a groove or projections, and wherein the at least one of the groove or projections is configured to releasably lock the hub against movement by the spring actuator.

11. The arrangement of claim 1 further comprising a trigger configured to release the hub of at least one of the sampling and analysis sites, and wherein the respective spring actuator of the at least one sampling and analysis site is configured to move the hub when the hub is released.

12. The arrangement of claim 11, wherein the trigger comprises a moveable arm, and wherein the hub of the at least one sampling and analysis site comprises a groove and the respective spring actuator of the at least one sampling and analysis site comprises a spring having a leg releasably mounted in the groove, and wherein the moveable arm is configured to displace the leg from the groove and the spring actuator of the at least one sampling and analysis site is configured to move the hub of the at least one sampling and analysis site when the moveable arm displaces the leg from the groove.

13. The arrangement of claim 12, wherein the moveable arm comprises an angular or arcuate ramp surface.

14. The arrangement of claim 12, wherein the housing comprises an opening for passage of the moveable arm, wherein the opening comprises a seal and wherein the seal comprises a solid flexible membrane, an apertured membrane in combination with a secondary seal, or a piercable membrane.

15. The arrangement of claim 11, wherein the trigger comprises a severable wire or fuse.

16. The arrangement of claim 1, wherein the arrangement is a disposable cartridge.

17. The arrangement of claim 1, further comprising a barcode or a chip, wherein the barcode or the chip comprises readable information and wherein the barcode or the chip is contained on or within the housing.

18. The arrangement of claim 17, wherein the readable information comprises at least one of: calibration information, algorithm information, software code, and accuracy verification information.

19. The arrangement of claim 1, wherein at least one of the sampling and analysis sites comprises a control corresponding to a predetermined analyte concentration.

20. The arrangement of claim 1, further comprising at least one light source and detector, wherein the at least one light source and detector are configured to interrogate each analyte quantification member.

21. The arrangement of claim 20, wherein the analyte quantification members are configured to move to facilitate the creation of a list of unused analyte quantification members or to align an analyte quantification member with the at least one light source and detector for analysis.

22. The arrangement of claim 20, wherein the at least one light source and detector are configured to move to create a list of unused analyte quantification members or to align an analyte quantification member with the at least one light source and detector for analysis.

23. The arrangement of claim 22, wherein the at least one light source and detector are mounted on a moveable indexing arm.

24. The arrangement of claim 20, the arrangement further comprising a plurality of light transmitting elements in optical communication with the at least one light source and the analyte quantification members, wherein the at least one light source and detector and the analyte quantification members are fixed relative to each other, wherein the detector is positioned to receive light reflected off each analyte quantification member, and wherein the detector comprises a plurality of sections, each section designated to receive light reflected off of a respective one of the analyte quantification members.

25. The arrangement of claim 20, wherein the at least one light source and detector, and the analyte quantification members, are fixed relative to each other, and further comprising a plurality of light transmitting elements in optical communication with the at least one light source and analyte quantification members, wherein the detector comprises a plurality of discrete detector elements, and wherein each of the plurality of discrete detector elements is positioned to receive light reflected off of a respective one of the analyte quantification members.

26. The arrangement of claim 1, wherein the spring actuator of at least one of the sampling and analysis sites is configured to move the hub and the skin-penetration member in an arcing movement toward the skin of the user.

27. The arrangement of claim 1, wherein the arrangement further comprises a cartridge and the cartridge comprises the plurality of sampling and analysis sites.

28. The arrangement of claim 1, wherein the arrangement has an annular shape.

29. An integrated body fluid sampling and analysis device comprising the arrangement of claim 1.

30. The integrated device of claim 29, further comprising a detector in optical communication with at least one analyte quantification member.

31. The integrated device of claim 30, wherein the detector comprises at least one complementary metal oxide semiconductor (CMOS)-based detector element.

32. The integrated device of claim 30, wherein the detector comprises at least one linear or area array of CMOS-based detector elements.

33. The integrated device of claim 30, wherein the housing is configured to move to present a new skin-penetration member, spring actuator and analyte quantification member after the performance of a preceding sampling and analysis event.

34. The integrated device of claim 29, wherein the device is configured for one or more of hand-held operation and operation while being worn.

35. The integrated device of claim 29, wherein the device is configured for one or more of fingertip sampling and alternate site sampling.

36. An arrangement comprising:
 a housing;
 a plurality of sampling and analysis sites contained within the housing, each of the sampling and analysis sites comprising:
  a skin-penetration member having a first end configured to pierce skin, and an inner lumen in communication with the first end;
  an actuator configured to drive the skin-penetration member into skin of a user;
  a hub, wherein the skin-penetration member and the actuator are attached to the hub;
  a pin, wherein the hub is configured to rotate around the pin; and
  an analyte quantification member disposed on or within the hub, wherein the analyte quantification member is in fluid communication with the inner lumen of the skin-penetration member.

37. The arrangement of claim 36, wherein the arrangement further comprises a cartridge and the cartridge comprises the plurality of sampling and analysis sites.

38. The arrangement of claim 36, wherein the actuator of at least one of the sampling and analysis sites is configured to move the hub and the skin-penetration member in an arcing movement toward the skin of the user.

39. The arrangement of claim 36, wherein the arrangement has an annular shape.

40. The arrangement of claim 36, wherein the arrangement is a disposable cartridge.

* * * * *